US010132776B2

United States Patent
Sivan et al.

(10) Patent No.: US 10,132,776 B2
(45) Date of Patent: Nov. 20, 2018

(54) PH GRADIENTS CONTROLLED BY ELECTROLYSIS, AND THEIR USE IN ISOELECTRIC FOCUSING

(71) Applicant: Technion Research & Development Foundation Limited, Haifa (IL)

(72) Inventors: Uri Sivan, Haifa (IL); Elad Brod, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 230 days.

(21) Appl. No.: 15/055,601

(22) Filed: Feb. 28, 2016

(65) Prior Publication Data

US 2016/0178578 A1    Jun. 23, 2016

Related U.S. Application Data

(62) Division of application No. 12/675,794, filed as application No. PCT/IL2008/001159 on Aug. 26, 2008, now Pat. No. 9,274,082.
(Continued)

(51) Int. Cl.
*G01N 27/447* (2006.01)
*C02F 1/461* (2006.01)

(52) U.S. Cl.
CPC . *G01N 27/44795* (2013.01); *G01N 27/44717* (2013.01); *G01N 27/44743* (2013.01);
(Continued)

(58) Field of Classification Search
CPC .......... C02F 1/4618; C02F 2001/46157; C02F 2201/46115; C02F 2201/4612;
(Continued)

(56) References Cited

U.S. PATENT DOCUMENTS 4,670,119 A * 6/1987 Hurd ................ G01N 27/44795
204/548
4,868,130 A    9/1989 Hargreaves
(Continued)

FOREIGN PATENT DOCUMENTS

AU    2008293381    3/2009
CN    1462368    12/2003
(Continued)

OTHER PUBLICATIONS

Examination Report Under Sections 12 & 13 of the Patents Acts, 1970 and the Patents Rules, 2003 dated Dec. 6, 2017 From the Government of India, Intellectual Property India, Patents, Designs, Trade Marks, Geographical Indications Re. Application No. 623/MUMNP/2010. (6 Pages).
(Continued)

*Primary Examiner* — Maris R Kessel
*Assistant Examiner* — Joshua L Allen

(57) ABSTRACT

A specified proton concentration in a volume (80) is produced by passing a controlled electrophoresis current through an adjacent electrophoresis volume (28) between a working electrode (26) and a counter electrode (24). An array of such volumes with specified proton concentration is used to provide the pH gradient for isoelectric focusing.

9 Claims, 20 Drawing Sheets

US 10,132,776 B2

Page 2

Related U.S. Application Data

(60) Provisional application No. 61/039,257, filed on Mar. 25, 2008, provisional application No. 60/935,698, filed on Aug. 27, 2007.

(52) U.S. Cl.
CPC .. *C02F 1/4618* (2013.01); *C02F 2001/46157* (2013.01); *C02F 2201/4612* (2013.01); *C02F 2201/46115* (2013.01); *C02F 2201/46125* (2013.01)

(58) Field of Classification Search
CPC .... C02F 2201/46125; G01N 27/44717; G01N 27/44743; G01N 27/44795
USPC ................. 204/459, 548, 610, 644
See application file for complete search history.

(56) References Cited

U.S. PATENT DOCUMENTS

| | | | | |
|---|---|---|---|---|
| 4,900,414 | A * | 2/1990 | Sibalis | B01D 57/02 204/457 |
| 5,091,070 | A | 2/1992 | Bauer et al. | |
| 5,110,434 | A | 5/1992 | Zhu et al. | |
| 5,646,001 | A | 7/1997 | Terstappen et al. | |
| 6,296,752 | B1 * | 10/2001 | McBride | B03C 5/026 204/450 |
| 6,824,740 | B1 | 11/2004 | Sheldon, III et al. | |
| 7,166,202 | B2 | 1/2007 | Bukshpan et al. | |
| 8,366,899 | B2 | 2/2013 | Albrecht et al. | |
| 2001/0023825 | A1 | 9/2001 | Frumin et al. | |
| 2003/0102215 | A1 | 6/2003 | Bukshpan et al. | |
| 2004/0101973 | A1 | 5/2004 | Weber | |
| 2004/0231986 | A1 * | 11/2004 | Rossier | G01N 27/44773 204/450 |
| 2004/0251136 | A1 * | 12/2004 | Lean | G01N 27/44713 204/456 |
| 2005/0126911 | A1 | 6/2005 | Anderson et al. | |
| 2005/0189237 | A1 | 9/2005 | Sano | |
| 2005/0284762 | A1 | 12/2005 | Astorga-Wells et al. | |
| 2006/0029978 | A1 | 2/2006 | O'Neill et al. | |
| 2006/0137603 | A1 | 6/2006 | Bukshpan | |
| 2006/0169575 | A1 | 8/2006 | Sumita | |
| 2009/0008268 | A1 | 1/2009 | Salathe et al. | |
| 2010/0307920 | A1 | 12/2010 | Sivan et al. | |
| 2012/0138468 | A1 | 6/2012 | Sivan et al. | |
| 2012/0145548 | A1 | 6/2012 | Sivan et al. | |
| 2013/0140182 | A1 | 6/2013 | Paulus et al. | |

FOREIGN PATENT DOCUMENTS

| | | |
|---|---|---|
| CN | 1549924 | 11/2004 |
| CN | 1558460 | 12/2004 |
| CN | 101294930 | 10/2008 |
| EP | 688395 | 8/2006 |
| EP | 2193100 | 6/2010 |
| EP | 2559666 | 2/2013 |
| JP | 2002-265494 | 9/2002 |
| JP | 2006-213932 | 8/2006 |
| JP | 2006-247640 | 9/2006 |
| JP | 2007-190548 | 8/2007 |
| WO | WO 91/17815 | 11/1991 |
| WO | WO 02/25263 | 3/2002 |
| WO | WO 03/008977 | 1/2003 |
| WO | WO 2005/021841 | 3/2005 |
| WO | WO 2007/093395 | 8/2007 |
| WO | WO 2008/112253 | 9/2008 |
| WO | WO 2008/131328 | 10/2008 |
| WO | WO 2009/002459 | 12/2008 |
| WO | WO 2009/027970 | 3/2009 |
| WO | WO 2011/021196 | 2/2011 |

OTHER PUBLICATIONS

Requisition by the Examiner dated Mar. 8, 2016 From the Canadian Intellectual Property Office Re. Application No. 2,770,270.
Communication Pursuant to Article 94(3) EPC dated Feb. 22, 2017 From the European Patent Office Re. Application No. 10757843.7. (6 Pages).
Requisition by the Examiner dated Feb. 15, 2017 From the Canadian Intellectual Property Office Re. Application No. 2,770,270. (6 Pages).
Advisory Action Before the Filing of an Appeal Brief dated Jul. 31, 2015 From the US Patent and Trademark Office Re. U.S. Appl. No. 12/675,794.
Communication Pursuant to Article 94(3) EPC dated Jul. 20, 2010 From the European Patent Office Re. Application No. 08789831.8.
Communication Pursuant to Article 94(3) EPC dated Mar. 24, 2011 From the European Patent Office Re. Application No. 08789831.8.
Communication Pursuant to Article 94(3) EPC dated Jul. 26, 2011 From the European Patent Office Re. Application No. 08789831.8.
Communication Pursuant to Article 94(3) EPC dated Sep. 28, 2010 From the European Patent Office Re. Application No. 08789831.8.
Communication Relating to the Results of the Partial International Search dated Dec. 20, 2010 From the International Searching Authority Re. Application No. PCT/IL2010/000672.
Dismissal of Amendment dated Mar. 14, 2014 From the Japanese Patent Office Re. Application No. 2010-522513 and Its Translation Into English.
Examiner's Report dated Feb. 27, 2012 From the Australian Government, IP Australia Re. Application No. 2008293381.
International Preliminary Report on Patentability dated Mar. 1, 2012 From the International Bureau of WIPO Re. Application No. PCT/IL2010/000672.
International Preliminary Report on Patentability dated Mar. 1, 2012 From the International Bureau of WIPO Re. Application No. PCT/IL2011/000671.
International Preliminary Report on Patentability dated Mar. 2, 2010 From the International Bureau of WIPO Re. Application No. PCT/IL2008001159.
International Search Report and the Written Opinion dated Apr. 7, 2009 From the International Searching Authority Re. Application No. PCT/IL2008/001159.
International Search Report and the Written Opinion dated Dec. 10, 2010 From the International Searching Authority Re. Application No. PCT/IL2010/000671.
International Search Report and the Written Opinion dated Mar. 24, 2011 From the International Searching Authority Re. Application No. PCT/1L2010/000672.
Invitation Pursuant to Rule 62a(1) EPC dated Nov. 23, 2012 From the European Patent Office Re. Application No. 12177368.3.
Notice of Reason for Rejection dated Jun. 6, 2014 From the Japanese Patent Office Re. Application No. 2012-525252 and Its Translation Into English.
Notice of Reason for Rejection dated Jan. 7, 2014 From the Japanese Patent Office Re. Application No. 2012-525253 and Its Translation Into English.
Notice of Reason for Rejection dated Sep. 26, 2014 From the Japanese Patent Office Re. Application No. 2010-522513 and Its Translation Into English.
Notice of the Reason for Rejection dated Dec. 16, 2014 From the Korean Intellectual Property Office Re. Application No. 10-2010-7006740 and Its Translation Into English.
Notification of Office Action dated Jan. 9, 2014 From the State Intellectual Property Office of the People's Republic of China Re. Application No. 201080036972.6 and Its Translation Into English.
Notification of the Office Action dated May 8, 2014 From the State Intellectual Property Office of the People's Republic of China Re. Application No. 201080036971.1 and Its Translation Into English.
Notification of the Office Action dated Sep. 18, 2013 From the State Intellectual Property Office of the People's Republic of China Re. Application No. 201080036971.1 and Its Translation Into English.
Office Action dated Jan. 14, 2013 From the Israel Patent Office Re. Application No. 204182 and Its Translation Into English.
Office Action dated Nov. 16, 2015 From the Israel Patent Office Re. Application No. 218168 and Its Translation Into English.

(56) References Cited

OTHER PUBLICATIONS

Office Action dated Feb. 20, 2014 From the State Intellectual Property Office of the People's Republic of China Re. Application No. 201210450797.6 and Its Translation Into English.
Official Action dated Jun. 6, 2013 From the US Patent and Trademark Office Re. U.S. Appl. No. 12/675,794.
Official Action dated Sep. 10, 2013 From the US Patent and Trademark Office Re. U.S. Appl. No. 13/669,023.
Official Action dated Jul. 11, 2014 From the US Patent and Trademark Office Re. U.S. Appl. No. 12/675,794.
Official Action dated Aug. 13, 2014 From the US Patent and Trademark Office Re. U.S. Appl. No. 13/390,352.
Official Action dated Mar. 13, 2015 From the US Patent and Trademark Office Re. U.S. Appl. No. 12/675,794.
Official Action dated Jan. 16, 2014 From the US Patent and Trademark Office Re. U.S. Appl. No. 13/390,352.
Official Action dated Nov. 16, 2012 From the US Patent and Trademark Office Re. U.S. Appl. No. 12/675,794.
Official Action dated Jan. 23, 2014 From the US Patent and Trademark Office Re. U.S. Appl. No. 13/390,539.
Official Decision of Rejection dated Mar. 14, 2014 From the Japanese Patent Office Re. Application No. 2010-522513 and Its Translation Into English.
Partial European Search Report and the European Search Opinion dated Mar. 5, 2013 From the European Patent Office Re. Application No. 12177368.3.
Patent Examination Report dated Jun. 5, 2014 From the Australian Government, IP Australia Re. Application No. 2010286046.
Patent Examination Report dated Jul. 30, 2014 From the Australian Government, IP Australia Re. Application No. 2010286047.
Requisition by the Examiner and Examination Search Report dated Oct. 21, 2014 From the Canadian Intellectual Property Office Re. U.S. Pat. No. 2,697,649.
Requisition by the Examiner dated Jun. 9, 2015 From the Canadian Intellectual Property Office Re. Application No. 2,697,649.
Restriction Official Action dated Oct. 7, 2013 From the US Patent and Trademark Office Re. Application No. 13/390,352.
Restriction Official Action dated Nov. 12, 2013 From the US Patent and Trademark Office Re. U.S. Appl. No. 13/390,539.
Restriction Official Action dated Sep. 19, 2012 From the US Patent and Trademark Office Re. U.S. Appl. No. 12/675,794.
Search Report dated Sep. 18, 2013 From the State Intellectual Property Office of the People's Republic of China Re. Application No. 201080036971.1 and Its Translation Into English.
Search Report dated Feb. 20, 2014 From the State Intellectual Property Office of the People's Republic of China Re. Application No. 201210450797.6 and Its Translation Into English.
Translation of Notice of Reason for Rejection dated Jul. 2, 2013 From the Japanese Patent Office Re. Application No. 2010-522513.
Translation of Notice of Reason for Rejection dated Sep. 20, 2013 From the Japanese Patent Office Re. Application No. 2012-525252.
Translation of Notice of Reason for Rejection dated Jul. 27, 2012 From the Japanese Patent Office Re. Application No. 2010-522513.
Translation of Notification of Office Action dated Jul. 29, 2013 From the State Intellectual Property Office of the People's Republic of China Re. Application No. 201080036972.6.
Translation of Office Action dated May 2, 2012 From the State Intellectual Property Office of the People's Republic of China Re. Application No. 200880114690.6.
Translation of Office Action dated Nov. 9, 2011 From the State Intellectual Property Office of the People's Republic of China Re. Application No. 200880114690.6.
Translation of Search Report dated Jul. 29, 2013 From the State Intellectual Property Office of the People's Republic of China Re. Application No. 201080036972.6.
Britz-McKibbin et al. "Selective Focusing of Catecholamines and Weakly Acidic Compounds by Capillary Electrophoresis Using a Dynamic pH Junction", Analytical Chemistry, XP002611194, 72(6): 1242-1252, Mar. 15, 2000. p. 1250, col. 1, Line 22—p. 1251, col. 1, Line 1, Fig.9.
De Jong et al. "Membranes and Microfluidics: A Review", Lab on a Chip, 6(9): 1125-1139, Sep. 2006.
Huang et al. "Capillary Isoelectric Focusing Without Carrier Ampholytes", Analytical Chemistry, XP002584974, 72(19): 4758-4761, Oct. 1, 2000. Abstract, Fig.1.
Pabst et al. "Separation of Protein Charge Variants With Induced pH Gradients Using Anion Exchange Chromatographic Columns", Biotechnology Progress, XP002611195, 24(5): 1096-1106, Sep. 2008. Abstract, p. 1100, col. 1, Lines 12-16.
Wu et al. "Isoelectric Focusing Sample Injection for Capillary Electrophoresis of Proteins", Electrophoresis, XP002611196, 26(3): 563-570, Feb. 2005. Abstract, p. 565, col. 2, Last § —p. 566, col. 1, Last §, p. 567, col. 1, Line 17—col. 2, Line 11, Fig.3B.
Wu et al. "Miniaturization of Capillary Isoelectric Focusing", Electrophoresis, XP003008375, 22: 3968-3971, Jan. 1, 2001. Abstract, p. 3669, col. 2, Line 1—p. 3970, col. 1, Last Line, Figs.1, 3, 4.
Examination Report Under Sections 12 & 13 of the Patents Act, 1970 and the Patents Rules, 2003 dated Aug. 2, 2018 From the Government of India, Intellectual Property India, Patents, Designs, Trade Marks, Geographical Indications Re. Application No. 353/MUMNP/2012. (6 Pages).
Invitation Pursuant to Rule 137(4) EPC and Article 94(3) EPC dated Jun. 22, 2018 From the European Patent Office Re. Application No. 10760443.1. (2 Pages).

\* cited by examiner vii viii

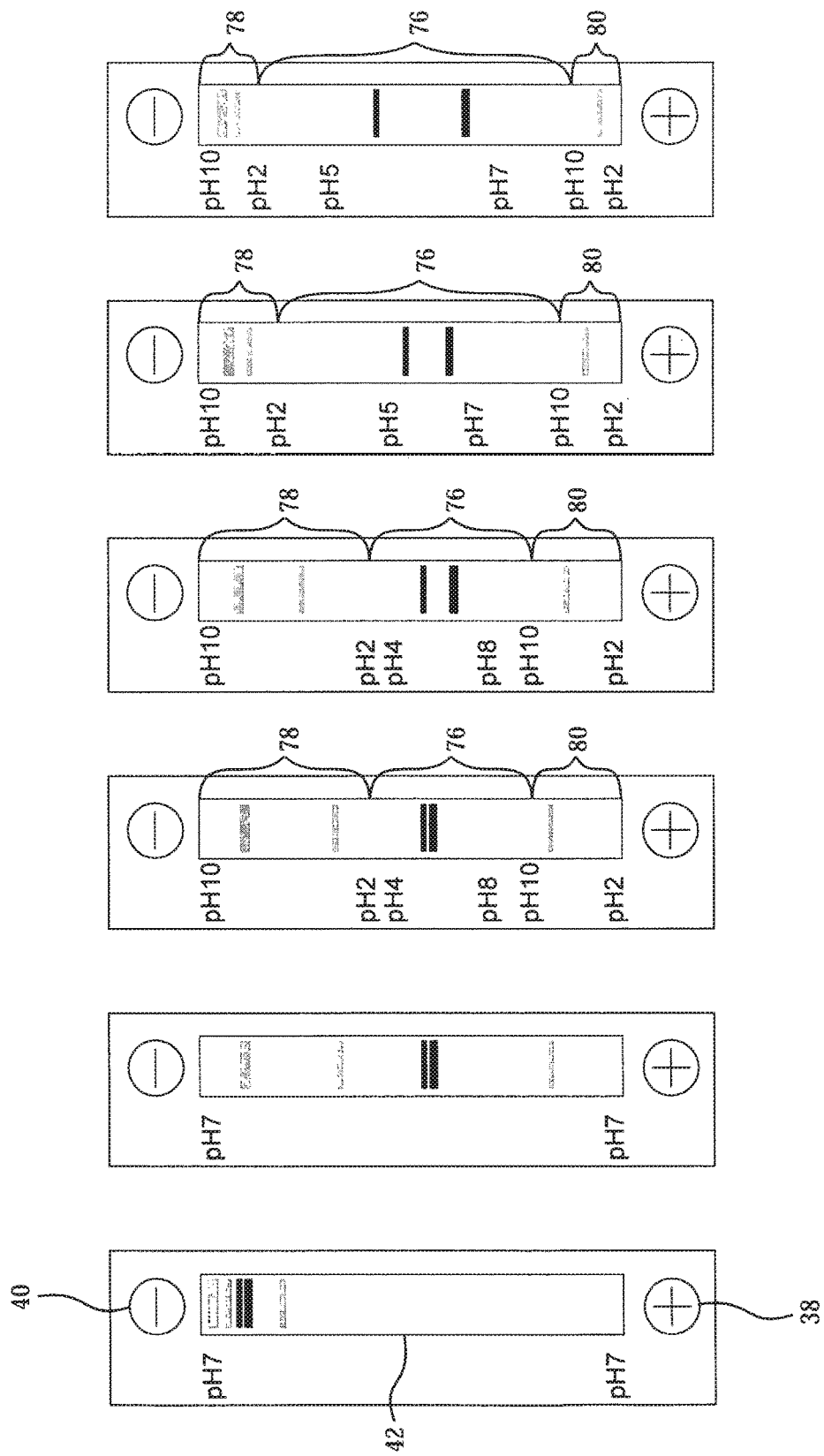

PH GRADIENTS CONTROLLED BY ELECTROLYSIS, AND THEIR USE IN ISOELECTRIC FOCUSING

RELATED APPLICATIONS

This application is a division of U.S. patent application Ser. No. 12/675,794 filed on Aug. 25, 2010, which is a National Phase of PCT Patent Application No. PCT/IL2008/001159 having International Filing Date of Aug. 26, 2008, which claims the benefit of priority of U.S. Provisional Patent Application Nos. 60/935,698, filed on Aug. 27, 2007 and 61/039,257, filed on Mar. 25, 2008.

The contents of the above applications are all incorporated by reference as if fully set forth herein in their entirety.

FIELD AND BACKGROUND OF THE INVENTION

The present invention, in some embodiments, relates to the field of molecular interactions, and particularly to methods and devices useful in producing local concentration of protons, proton concentration gradients and desired proton concentration topographies in an environment (e.g., a solution, a gel, or the like) including an electrolyte. Some embodiments of the invention also relate to the field of analyte separation and isoelectric focusing. Some embodiments of the invention also relate to the field of data display.

Isoelectric focusing is an analytical technique for separating molecules in an analyte sample by taking advantage of the differing ionic properties of the molecules.

Isoelectric focusing is performed in a gel (usually of materials such as polyarylamide polyacrylamide, starch or agarose) having an immobilized proton concentration gradient, generally the proton concentration gradient changing from higher to lower pH in a given direction.

The analyte is loaded onto some location on the gel. The charge of each different molecule changes in response to the ambient proton concentration according to the acidity (pKa) of the various functional groups of the molecule.

An electric potential is applied parallel to the proton concentration gradient between an isoelectric focusing anode and isoelectric focusing cathode. Molecules having a net positive charge migrate through the gel towards the anode while molecules having a net negative charge migrate through the gel towards the cathode. The opposite, positively charge ions (cations) migrate towards the cathode and negatively charged ions (anions) migrate towards the anode.

As the molecules migrate, the ambient pH changes to reduce the net charge on the molecule until the molecule reaches an isoelectric point (pI) where, due to the ambient pH, the net charge on the molecule is zero so that the molecule stops migrating due to the electric potential. If a molecule "overshoots" the isoelectric point, the molecule reverses direction.

In such a way, isoelectric focusing focuses molecules having the same pI into very narrow well-defined volumes of the gel.

Isoelectric focusing is exceptionally useful for the analysis of proteins as proteins are characterized by having many functional groups of different acidities.

Isoelectric focusing suffers from a number of disadvantages. To have sufficient resolution, it is often necessary to have a number of different gels having different proton concentration gradients spanning different ranges of proton concentration gradients, increasing costs and creating a logistical problem. Automated manipulation of fragile gels is difficult to implement. Gels having immobilized proton concentration gradients are generally expensive and may suffer from batch to batch reproducibility. Analysis of some analytes may suffer from a sieving effect as large proteins may have difficulty migrating through pores in the gels. Isoelectric focusing may be slow due to the slow migration of the analyte molecules.

It would be advantageous to be able to perform isoelectric focusing with fewer disadvantages of the methods known in the art.

SUMMARY OF THE INVENTION

The invention relates, in some embodiments, to the field of molecular interactions, and particularly to proton concentration topographies, methods and devices useful in producing specified local concentrations of protons and specified proton concentration topographies in an environment including an electrolyte that, in some embodiments, are mutable and may be changed as desired or that are temporally variable.

Some embodiments of the present invention provide for isoelectric focusing that is devoid of at least some of the disadvantages of the methods known in the art.

Some embodiments of the present invention provide for the display of data.

In some embodiments, the invention provides a device comprising a plurality of independently controllable cells, arranged for example in a one- or two-dimensional array, and an environment including an electrolyte. Each cell is configured to independently produce a specified proton concentration in an associated volume of the environment. When the device is activated, a user can use the cells to produce a desired one- or two-dimensional proton concentration topography in the environment, where each volume of the environment has a specified proton concentration that is substantially not dependent on the proton concentration in adjacent volumes.

In some embodiments, the proton concentration topography is mutable. In some such embodiments, a user may choose to change the proton concentration in some or all of the volumes, and consequently the proton concentration topography, by controlling the cells. In some embodiments, the user may choose to change the proton concentration in some or all of the volumes as a function of time, and consequently the proton concentration topography as a function of time.

Thus, according to an aspect of some embodiments of the invention there is provided proton concentration topography, comprising: a) an environment including an electrolyte, the environment divided into a plurality of neighboring discrete volumes; b) between any two neighboring volumes, an interface volume; and c) each volume having a specified proton concentration.

Depending on the embodiment, the volumes are arranged in one dimension, for example constituting a one-dimensional array of volumes, in two dimensions, for example constituting a two-dimensional array of volumes, or arranged in three dimensions, constituting a three-dimensional array.

According to some embodiments, in a given direction through the environment the rate of change of proton concentration between neighboring volumes is substantially monotonous.

According to some embodiments, in a given direction through the environment, the rate of change of proton concentration between neighboring volumes varies.

According to some embodiments, the proton concentration topography is controllably mutable. According to some embodiments, the proton concentration topography is controllably mutable as a function of time.

According to an aspect of some embodiments of the invention there is provided a method of producing a specified proton concentration topography in an environment including an electrolyte, comprising:
 a) providing a plurality of independently controllable cells, each cell configured to produce a specified proton concentration in an associated volume of an environment including an electrolyte, for example by electrolysis of components of the environment
 b) contacting an environment including an electrolyte with the plurality of cells so as to divide the environment into a plurality of neighboring discrete volumes, each volume associated with a cell;
 c) specifying a desired proton concentration topography; and
 d) activating each cell of the plurality of cells, so as to produce a specified proton concentration in each volume associated with a cell in the environment,
wherein the specified proton concentrations produced in each volume collectively constitute the specified proton concentration topography.

According to an aspect of some embodiments of the invention there is provided a device for the production of a proton concentration topography in an environment including an electrolyte, comprising:
 a) a plurality of independently controllable cells, each cell configured to produce a specified proton concentration in an associated volume of an environment including an electrolyte, for example by electrolysis of a component of the environment, substantially independently of other the cells; and
 b) a container functionally associated with the plurality of cells configured to contain an environment including an electrolyte, the container configured to allow production of the specified proton concentration by a cell in an associated volume of an environment contained in the container.

According to an aspect of some embodiments of the invention there is provided a method for producing a specified proton concentration in an environment including an electrolyte, comprising:
 a) providing an environment including an electrolyte;
 b) contacting a working electrode and a counter electrode with the environment so that:
  a first side of the working electrode faces the counter electrode to define an electrolysis volume of the environment between the working electrode and the counter electrode, and
  a second side of the working electrode faces a second volume of the environment;
 c) specifying a desired proton concentration;
 d) passing a current between the working electrode and the counter electrode so as to electrolyze components of the environment to generate electrolysis products (e.g., ions) in the electrolysis volume; and
 e) transferring at least some of the electrolysis products to the second volume, thereby producing a proton concentration in the second volume of the environment
wherein the current is such that the proton concentration produced in the second volume is the specified proton concentration. According to some embodiments, the working electrode is permeable to the passage of electrolysis products therethrough (e.g., is made of mesh) and the transferring includes allowing electrolysis products generated in the electrolysis volume to pass through the working electrode into the second volume, thereby producing the proton concentration in the second volume.

According to an aspect of some embodiments of the invention there is provided a device for producing a specified proton concentration in an environment including an electrolyte, comprising:
 a) a working electrode; and
 b) a counter electrode,
 the working electrode and the counter electrode arranged so that:
  a first side of the working electrode faces the counter electrode to define an electrolysis volume between the working electrode and the counter electrode, and
  a second side of the working electrode faces a volume of a container, the container configured to contain an environment including an electrolyte,
wherein the electrolysis volume is in fluid communication with the volume of the container. According to some embodiments, the working electrode is permeable to the passage of electrolysis products therethrough (e.g., is made of mesh) to allow electrolysis products generated in the electrolysis volume to pass through the working electrode into the second volume.

According to an aspect of some embodiments of the invention, there is provided a method of analyzing an analyte using isoelectric focusing, comprising:
 a) placing an analyte suitable for analysis by isoelectric focusing in an environment including an electrolyte;
 b) producing a non-immobilized proton concentration topography in the environment;
 c) applying a potential difference to the environment; and
 d) observing locations of components of the analyte in the environment in relation to the proton concentration topography and the potential difference
thereby analyzing the analyte using isoelectric focusing. According to some embodiments, the non-immobilized proton concentration topography is mutable.

According to an aspect of some embodiments of the invention, there is provided a device useful in implementing the method of isoelectric focusing.

According to an aspect of some embodiments of the invention, there is provided a method of displaying data, comprising:
 a) providing a plurality of independently controllable cells, each cell configured to produce a specified proton concentration in an associated volume of an environment including an electrolyte, for example by electrolysis;
 b) contacting an environment with the plurality of cells so as to divide the environment into a plurality of neighboring discrete volumes, each of the plurality of discrete volumes associated with a cell, the environment including:
  an electrolyte, and
  a pH sensitive indicator having an appearance that is dependent on the proton concentration in the environment; and
 c) activating each cell of the plurality of cells, so as to produce a specified proton concentration in each associated volume of the environment
wherein the specified proton concentrations produced in each volume gives a specified appearance to the pH indicator; and
where the collective appearance of the pH indicator in the volumes is an image that constitutes a display of the data.

According to an aspect of some embodiments of the invention, there is provided a device useful in implementing the method of displaying data.

Unless otherwise defined, technical and/or scientific terms used herein have the same meaning as commonly understood by one of ordinary skill in the art to which the invention pertains. In case of conflict, the patent specification, including definitions, will control. The materials, methods, and examples disclosed herein are illustrative only and are not intended to be necessarily limiting.

As used herein, the terms "comprising", "including" and "having" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, the indefinite articles "a" and "an" mean "at least one" or "one or more" unless the context clearly dictates otherwise.

Unless the context dictates otherwise, the terms "generate" and "produce" or grammatical variants thereof are to be considered synonymous.

Herein, the terms "array of cells" and "electrode array" are in some instances used interchangeably.

Herein, the terms "analyte" and "material" are in some instances for the same concept in a different context. The term "analyte" generally refers to a material in an analytical context (e.g., analysis of the amount of the material present in a mixture) while the more general "material" refers, for example, to a material in a preparatory context.

BRIEF DESCRIPTION OF THE SEVERAL VIEWS OF THE DRAWINGS

Some embodiments of the invention are herein described, by way of example only, with reference to the accompanying figures. The description, together with the figures, makes apparent how embodiments of the invention may be practiced to a person having ordinary skill in the art. The figures are for the purpose of illustrative discussion of embodiments of the invention and no attempt is made to show structural details of an embodiment in more detail than is necessary for a fundamental understanding of the invention. For the sake of clarity, most objects depicted in the figures are not to scale.

In the Figures:

FIGS. 10A-10F schematically depict an embodiment of a method of the present invention for separating analytes in a mixture.

DESCRIPTION OF SOME EMBODIMENTS OF THE INVENTION

Figure 1A:
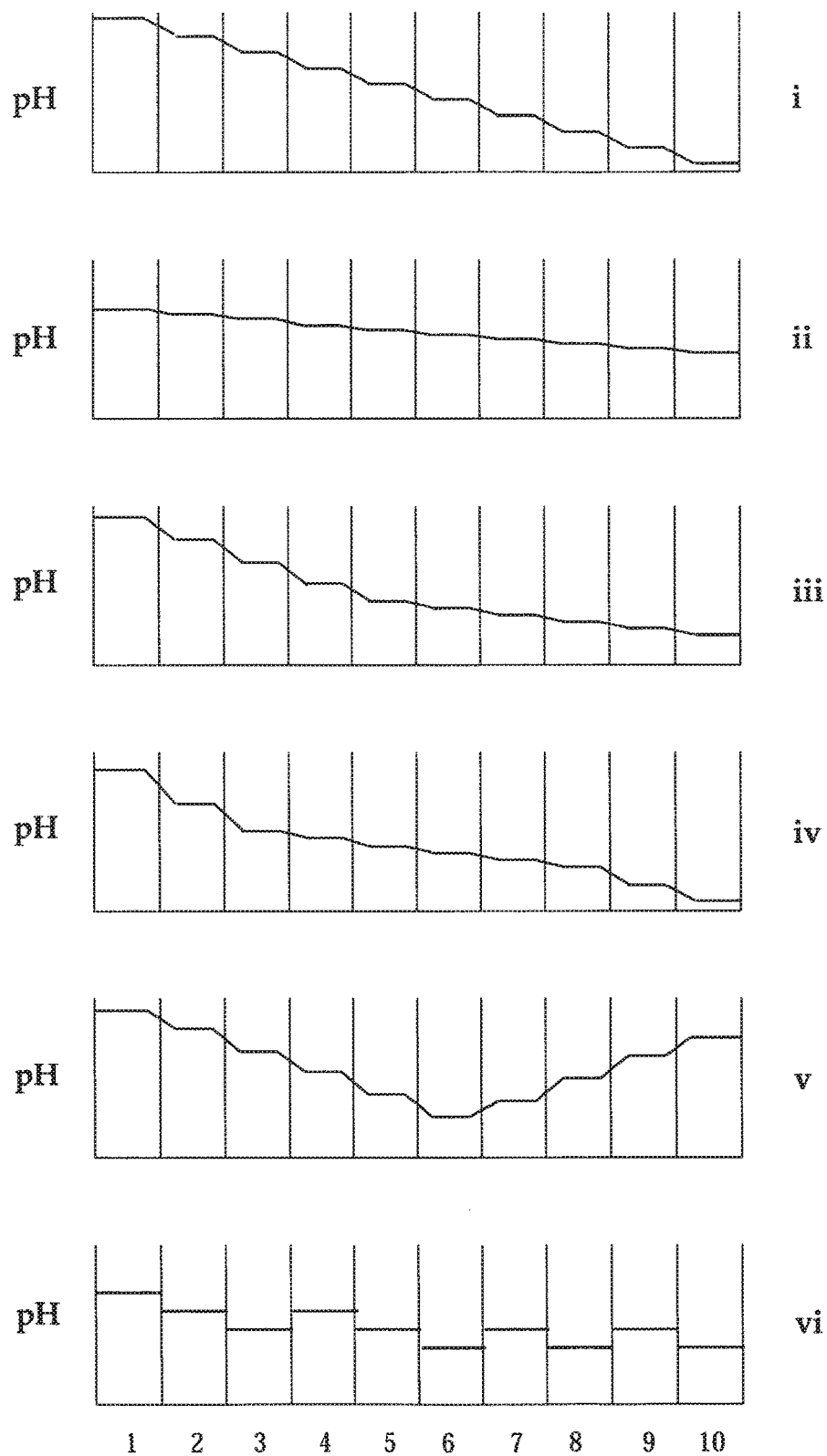
FIG. 1A schematically depicts various one-dimensional proton concentration topographies.

The invention, in some embodiments, is of proton concentration topographies as well as methods and devices for producing proton concentration topographies in an environment (e.g., a solution, gel or the like) including an electrolyte, generally environments having a low, negligible or non-existent buffering capacity. In some embodiments, the proton concentration topographies are non-immobilized, that is to say, are produced on-demand, when desired and as needed. In some embodiments, the produced proton concentration topographies are mutable, that is to say may be controllably changed at will or as a function of time. Some embodiments also relate to proton concentrations topographies in fluids such as liquids (as opposed, for example, to gels) that are useful, for example for isoelectric focusing and for purifying analytes. Some embodiments relate to or are useful for implementing isoelectric focusing. Some embodiments relate to or are useful for implementing isoelectric focusing in fluids. Some embodiments relate to or are useful for the display of data.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

As noted above, some embodiments of the invention relate to proton concentrations in an environment including an electrolyte. Such an environment allows the electrolytic generation of chemical entities, such as protons and hydroxyl anions that influence the proton concentration in the environment. Typical such environments include aqueous solutions and gels known in the art of isoelectric focusing and electrophoresis.

In the art, proton concentration gradients are known. For example, when a current is passed between two electrodes immersed in a non-buffered environment including an electrolyte, a monotonous proton concentration gradient is produced, a high proton concentration close to the anode that continuously and monotonously drops to a low proton concentration close to the cathode. Such proton concentration gradients are non-immobilized as these are produced only when desired. Such proton concentration gradients are also mutable as changing the electrical current passing between the electrodes changes the gradient.

In contrast, prior art isoelectric focusing methods are based on the use of non-mutable proton concentration gradients immobilized in a non-fluid environment such as a gel.

Some embodiments of the invention relate to proton concentration topographies in an environment. By proton concentration topography is meant the distribution of proton concentrations in the environment and as such includes the term "proton concentration gradient". However, while the term "proton concentration gradient" evokes a linear, continuous and monotonously changing proton concentration as a function of location, the term "proton concentration topography" has a broader meaning and includes distributions of proton concentrations in one-dimension (e.g., a line, curve, outline of a geometric figures such as a circle), in two-dimensions (e.g., a planar surface, a curved surface, a concave surface, a convex surface) and in three-dimensions. The term "proton concentration topography" includes topographies where in a given direction through the environment the rate of change of proton concentration is not continuous and/or not monotonous.

In some embodiment, a proton concentration is mutable and can be changed in a controlled fashion. Thus, in embodiments a proton concentration topography may have a desired arbitrary shape or pattern that, in embodiments, may be changed in a controllable fashion. In some embodiments, there is provided temporal and spatial control of proton concentration in an environment to allow generation of a controllable and adjustable proton concentration topographies, allowing generation of dynamic and complex proton concentration topographies that can be changed at will. In some embodiments, the control is with the use of an electronic or digital controller.

In some embodiments of the invention, a proton concentration topography is produced in a fluid environment, for example a liquid such as an aqueous solution. This allows implementation of isoelectric focusing and other methods using an ad hoc proton concentration topography produced in the fluid environment. Further, the use of a fluid environment in which to perform analyte separation allows for implementation of methods for preparing pure materials and not just for analysis of the mixture. An analyte mixture is separated using, for example, isoelectric focusing. A desired component, e.g. a single protein, is easily isolated from other components by extraction of the fluid including the component (e.g., with a pipette). This is much simpler and allows isolation of much greater amounts of material than the currently required excision of a volume of a gel. Thus, according to an aspect of some embodiments of the present invention there is provided a method of isolating a material (e.g., purifying or concentrating the material) from a mixture of materials (e.g., a polypeptide such as a protein or peptide from a mixture of polypeptides) comprising: a) performing isoelectric focusing of a mixture of materials including a desired material in a fluid environment; and b) subsequent to the isoelectric focusing, removing the fraction of the fluid environment including the desired material, thereby isolating the desired material from the mixture of materials.

Proton Concentration Topographies

In some embodiments the invention provides a proton concentration topography, comprising: a) an environment including an electrolyte, the environment divided into a plurality of neighboring discrete volumes; b) between any two neighboring volumes, an interface volume; and c) each volume having a specified proton concentration.

In some embodiments, the proton concentration topographies of the invention are discrete and not continuous. In some embodiments, the fact that the proton concentration topography is made up of a plurality of neighboring discrete volumes, each volume having a specified proton concentration means that each volume can be considered as a "pH-xel" (in analogy to a pixel for two-dimensional images).

In some embodiments, the volumes are arranged in one dimension, for example constituting a one-dimensional array of volumes, such as a line, curve or outline of a geometric figure such as a circle.

In some embodiments, the volumes are arranged in two dimensions, for example constituting a two-dimensional array of volumes, such as a hexagonal array where each non-edge volume is surrounded by six equidistant neighboring volumes or a square array where each non-edge volume is surrounded by four neighboring volumes arranged as a cross.

In some embodiments, the volumes are arranged in three dimensions, constituting a three-dimensional array.

In some embodiments, the movement of ions between two neighboring volumes is inhibited, for example by the interposition of a barrier impermeable to ions between two volumes. In some such embodiments, the interface volume is occupied by the barrier. Some such embodiments are exceptionally useful, for proton concentration topographies used for the display of data where it may be advantageous to have a sharp differentiation between the volumes (pH-xels).

In some embodiments, the movement of ions between two neighboring volumes is substantially uninhibited and d) each interface volume has a proton concentration related to the proton concentrations of the neighboring volumes defining the interface volume. Some such embodiments are exceptionally useful for proton concentration topographies used for implementation of isoelectric focusing where there is a need for analyte molecules to travel through the proton concentration topography until an isoelectric point is reached.

In some embodiments, in a given direction through the environment, the rate of change of proton concentration between neighboring volumes is substantially monotonous, for example is linear according to a molar or a pH scale.

In some embodiments, in a given direction through the environment, the rate of change of proton concentration between neighboring volumes varies, for example there are groups of neighboring volumes where the rate of change of proton concentration from volume to volume is much greater or much lesser than other groups, there are discontinuities or there are reversals in the rate of change.

In FIG. 1A are schematically depicted various embodiments of proton concentration topographies.

One dimensional topographies i-vi are all produced in a elongated vessel divided into ten neighboring discrete volumes where the proton concentration (in pH) of each volume and each interface volume is depicted with the help of graphs showing pH as a function of volume number.

In proton concentration topography i, the proton concentration monotonously increases at a constant (in pH units) at a high rate from a very low proton concentration in volume 1 to a very high concentration in volume 10. It is seen that in each volume, the pH is well-defined while in the interface volumes the proton concentration is a gradient related to the proton concentrations of the neighboring volumes defining the interface volume.

In proton concentration topography ii, the proton concentration monotonously increases at a constant (in pH units) at a low rate from a certain proton concentration in volume 1 to a somewhat higher proton concentration in volume 10.

In proton concentration topography iii, the proton concentration monotonously increases from volume 1 to volume 10 at a varying rate. From volume 1 to volume 4 the rate of increase in proton concentration is very high, while from volume 4 to volume 10 the rate of increase in proton concentration is relatively low.

In proton concentration topography iv, the proton concentration monotonously increases from volume 1 to volume 10 at a varying rate. From volume 1 to volume 2 the rate of increase in proton concentration is very high, from volume 3 to volume 8 the rate of increase in proton concentration is relatively low and from volume 8 to 10 the rate of increase in proton concentration is very high.

In proton concentration topography v, the proton concentration monotonously increases from volume 1 to volume 6 at a constant rate (in units of pH) and then monotonously decreases from volume 6 to 10 at a constant rate (in units of pH).

In proton concentration topography vi, the movement of ions between two neighboring volumes is inhibited, for example by the placement of impermeable barriers between any two volumes. It is seen that in such an embodiment, the interface volume is, in fact, occupied by the impermeable barrier and has no significant proton concentration.

Figure 1B:
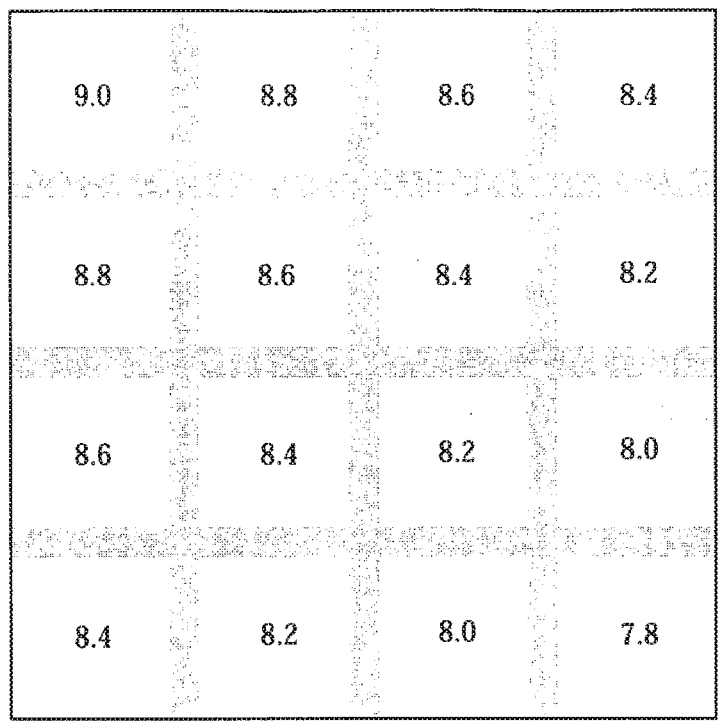
FIG. 1B schematically depicts various two-dimensional proton concentration topographies.
Figure 1B:
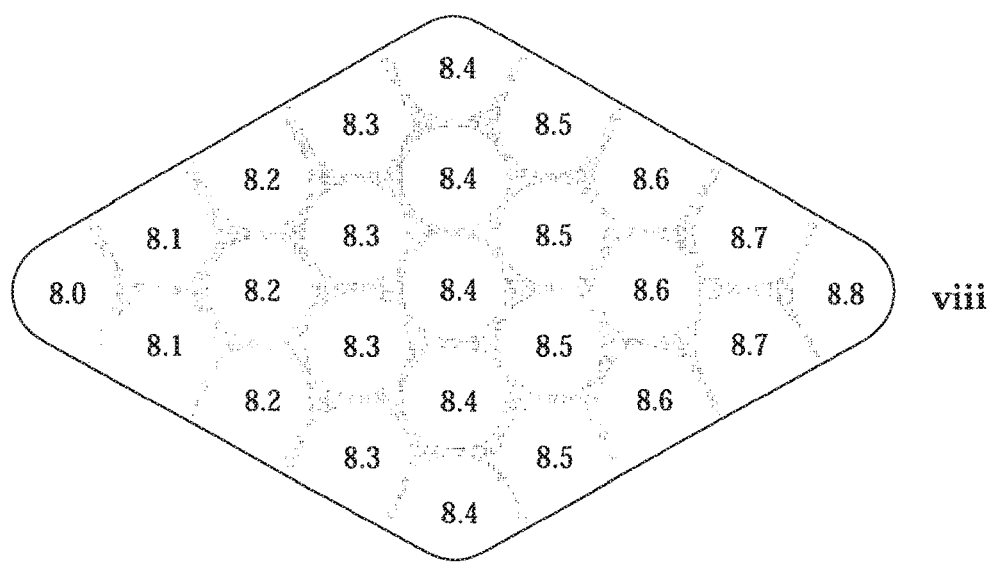

Proton concentration topographies vii and viii depicted in FIG. 1B are two-dimensional proton concentration topographies schematically depicted from above. In proton topographies vi and vii, interface volumes are depicted in grey. The proton concentration of each volume is written in units of pH in the center of the volume while the proton concentration of the interface volumes is defined by the neighboring volumes defining the interface volume.

Proton concentration topography vii comprises sixteen discrete neighboring volumes, arranged in a 4 volume by 4 volume square array where each non-edge volume is surrounded by four neighboring volumes arranged as a cross.

Proton concentration topography vii comprises 25 discrete neighboring volumes, arranged in a hexagonal array where each non-edge volume is surrounded by six equidistant neighboring volumes.

In some embodiments of the invention, a proton concentration topography is non-immobilized and is produced in an environment only when desired.

In some embodiments, the proton concentration topography is controllably mutable. In some embodiments, the proton concentration in at least one volume, preferably a plurality of volumes may be controllably changed so that the proton concentration topography is controllably mutable.

In some embodiments, the proton concentration topography is controllably mutable as a function of time. In some embodiments, the proton concentration in at least one volume, preferably a plurality of volumes, may be controllably changed as a function of time so that the proton concentration topography is controllably mutable as a function of time.

Methods for Producing a Proton Concentration Gradient

Any suitable method may be used to produce a proton concentration gradient. That said, some embodiments provide a method that may be used to produce a proton concentration gradient.

Some embodiments of the invention provide a method of producing a specified proton concentration topography in an environment including an electrolyte, comprising: a) providing a plurality of independently controllable cells, each cell configured to produce a specified proton concentration in an associated volume of an environment including an electrolyte, for example by electrolysis; b) contacting an environment including an electrolyte with the plurality of cells so as to divide the environment into a plurality of neighboring discrete volumes, each volume associated with a respective cell; c) specifying a desired proton concentration topography; and d) activating each cell of the plurality of cells, so as to produce a specified proton concentration in each volume associated with a cell of the environment, wherein the specified proton concentrations generated in each volume collectively constitute the specified proton concentration topography.

In some embodiments, e) subsequent to d, a desired proton concentration topography that is different than a previously defined proton concentration topography is specified; and f) where necessary, a cell of the plurality of cells is activated, to produce a different proton concentration in the associated volume of the environment, thereby changing the proton concentration topography to be the newly specified proton concentration topography.

In some embodiments, the method further comprises changing (stepwise or continuously) a proton concentration in at least one associated volume as a function of time, thereby changing the proton concentration topography as a function of time.

In some embodiments, the volumes are arranged in one dimension, for example constituting a one-dimensional array of volumes, such as a line, curve or outline of a geometric figure such as a circle.

In some embodiments, the volumes are arranged in two dimensions, for example constituting a two-dimensional array of volumes, such as a hexagonal array where each non-edge volume is surrounded by six equidistant neighboring volumes or a square array where each non-edge volume is surrounded by four neighboring volumes arranged as a cross.

In some embodiments, the volumes are arranged in three dimensions, constituting a three-dimensional array.

In some embodiments, the movement of ions between two the neighboring volumes is inhibited, for example by the interposition of physical barriers, e.g., sheets of impermeable material such as polyethylene or glass or other barriers impermeable to ions between two volumes. Some such embodiments are exceptionally useful when the method is used for the display of data where it may be advantageous to have a clear differentiation between the volumes.

In some embodiments, the movement of ions between two neighboring volumes is substantially uninhibited, for example the environment is a substantially homogenous (in the absence of different proton concentrations), for example a solution or a gel devoid of an immobilized proton concentration gradient. Some such embodiments are exceptionally useful when the method is used for implementation of isoelectric focusing where there is a need for analyte molecules to travel through the produced proton concentration topography until an isoelectric point is reached.

Devices for Producing a Proton Concentration Gradient

Any suitable device may be used to implement the method for producing a proton concentration gradient of the invention. That said, some embodiments of the invention provide a device that may be used to implement a method for producing a proton concentration gradient.

Some embodiments of the invention provide a device for the production of a proton concentration topography in an environment including an electrolyte, comprising: a) a plurality of independently controllable cells, each cell configured to produce a specified proton concentration in an associated volume of an environment including an electrolyte, for example by electrolysis of a component of the environment, substantially independently of the other cells; and b) a container functionally associated with the plurality of cells, the container configured to contain an environment including an electrolyte and configured to allow production of the specified proton concentration by the cell in a volume of the environment contained in the container, associated with the cell. In some embodiments, a plurality of cells is at least 2 cells, in some embodiments at least 5 cells, in some embodiments at least 10 cells, and in some embodiments at least 12 cells.

As noted above, in some embodiments, each volume associated with a cell may be considered as an independently controllable "pH-xel", where a respective cell may be used to produce a specified proton concentration in the associated volume. Such configuration of a device allows a desired proton concentration topography to be produced by the device, including a topography having arbitrary features, by changing the proton concentration in one or more of the associated volumes.

In some embodiments, the device further comprises an environment including an electrolyte contained within the container.

In some embodiments, the device is configured to allow substantially uninhibited movement of ions between two neighboring volumes. Some such embodiments are exceptionally useful when the device is used for implementation of isoelectric focusing where there is a need for analyte molecules to travel through the produced proton concentration topography until an isoelectric point is reached.

In some embodiments, the container has dimensions substantially larger than the dimensions of the volumes associated with the cells. In some such embodiments, a single large container is functionally associated with a plurality of cells, and the volumes of environment associated with the cells are physically continuous and defined by the proton concentration produced therein by an associated cell.

In some embodiments, the plurality of cells is arranged so that an environment held in the container is physically divided into a plurality of discrete neighboring volumes, each such volume being a volume associated with a cell, as described above. In such embodiments, the container may be considered a collection of subcontainers, each such subcontainer associated with a respective cell and in some embodiments at least partially defining the associated volume in which the respective cell produces a specified proton concentration. In some such embodiments, a subcontainer has dimensions of the order of a cell.

In some embodiments, the device further comprises barriers located between neighboring volumes and at least partially defining subcontainers, the barriers configured to inhibit the movement of ions between two neighboring volumes. Some such embodiments are exceptionally useful when the device is used for the display of data where it may be advantageous to have a sharp differentiation between the volumes. In such devices, neighboring volumes are generally close together and the barrier to ion movement is generally thin in relation to the size of the cells, for example, being less than 30%, less than 20% or even less than 10% of the distance between the centers of the two volumes which the barrier separates.

In some embodiments, the cells are arranged so that the associated volumes are arranged in one dimension, for example constituting a one-dimensional array of volumes, such as a line, curve or outline of a geometric figure such as a circle.

In some embodiments, the cells are arranged so that the associated volumes are arranged in two dimensions, for example constituting a two-dimensional array of volumes, such as a hexagonal array where each non-edge volume is surrounded by six equidistant neighboring volumes or a square array where each non-edge volume is surrounded by four neighboring volumes arranged as a cross.

In some embodiments, the cells are arranged so that the associated volumes are arranged in three dimensions, constituting a three-dimensional array.

In some embodiments, each cell is configured to change the specified proton concentration in the associated volume, in some embodiments substantially independently of the other cells. In some such embodiments, such configuration allows a desired proton concentration topography to be produced, for example a topography having arbitrary features, by changing the proton concentration in one or more of the associated volumes.

In some embodiments, each cell is configured to change the specified proton concentration in the associated volume as a function of time, in some embodiments substantially independently of other the cells. In some such embodiments, such configuration allows a produced proton concentration topography to be temporally variable.

In some embodiments, a device is configured to allow passage of an individually controllable electrical current through each of the cells when an environment including an electrolyte fills the container. In some such embodiments, such configuration allows a specified proton concentration topography to be produced.

In some embodiments, a device further comprises a controller configured to allow independent variation of the magnitude of an electrical current passing through each of the cells. In some embodiments, the controller is configured to vary the electrical input as a function of time, allowing the proton concentration topography to be changed as a function of time.

In some embodiments, the device further comprises a proton concentration sensor functionally associated with each of the cells, the proton concentration sensor configured to determine the value of a proton concentration in the volume associated with a cell and to report the determined value to a controller; and the controller is configured to change a magnitude of an electrical current passing through a cell in response to the reported value. In some embodiments, the device comprises a proton concentration sensor is used as a component of a feedback circuit to provide better control of a cell.

In some embodiments, the device further comprises a controller input component functionally associated with the controller, configured to allow a user to input a desired value for each of the cells, the desired value influencing the magnitude of an electrical current passing through the cell.

Figure 1C:
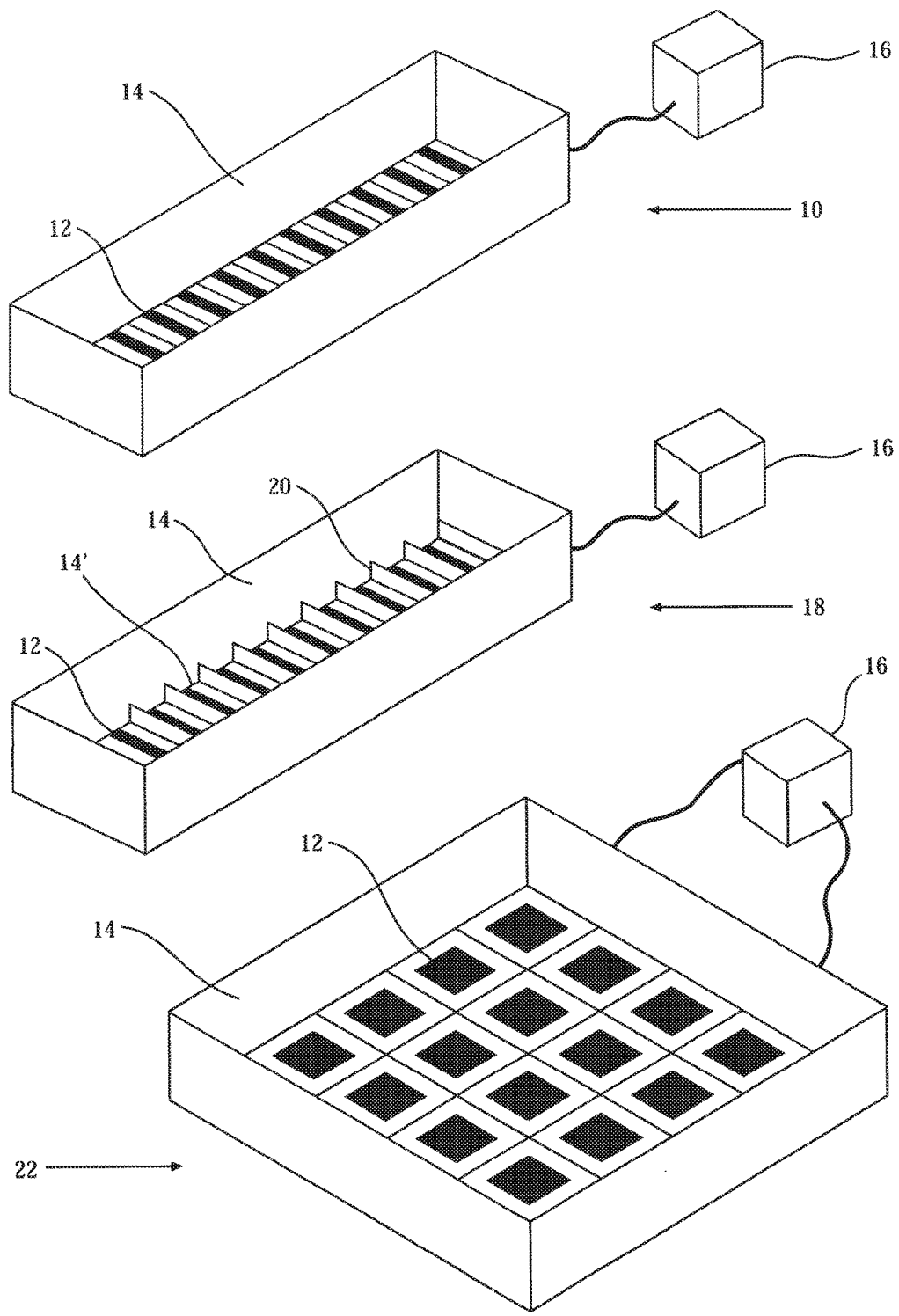
FIG. 1C schematically depicts, in perspective, devices for producing proton concentration topographies.

A number of embodiments of devices for producing a proton concentration gradient are depicted in FIG. 1C.

Device 10 comprises ten independently controllable cells 12 arranged in a line to constitute a linear area, each cell 12 configured to produce a specified proton concentration in an associated volume of an environment including an electrolyte held in container 14. The volumes associated with each cell 12 are the volume of environment held in container 14 proximal to that cell 12. As there are no barriers or other impediments between the associated volumes, device 10 is configured to allow substantially uninhibited movement of ions between neighboring volumes.

Device 10 comprises a controller 16 that is functionally associated with each of cells 12 and is used to control the proton concentration produced in the associated volume of each cell 12 by controlling the magnitude of an electric current passing through each cell 12. Controller 16 includes a controller input component allowing a user to input a desired proton concentration produced in an associated volume by each cell in order to specify a desired proton concentration topography. Device 10 may be used to produce many different proton concentration topographies, including proton topographies i, ii, iii, iv and v depicted in FIG. 1A.

Device 18 depicted in FIG. 1C is similar to device 10. However, container 14 is divided into ten subcontainers 14' by impermeable barriers 20.

In embodiments where container 14 is filled with a fluid environment including an electrolyte so that the level of fluid is lower than the height of barriers 20, the environment held in container 14 is divided into a plurality of physically discrete neighboring volumes where ion movement between neighboring volumes is inhibited. In such embodiments, each volume associated with a cell 12 is physically defined by a subcontainer 14'. In such embodiments, device 18 may be used to produce many different proton concentration topographies, including proton concentration topography vi depicted in FIG. 1A.

In some embodiments, container 14 is filled with a fluid environment including an electrolyte so that the level of fluid is higher than the height of barriers 20. In such embodiments, each volume associated with a cell 12 is only partially physically defined by a subcontainer 14'. In such embodiments, device 18 may be used to produce many different proton concentration topographies, including proton topographies i, ii, iii, iv and v depicted in FIG. 1A.

Device 22 depicted in FIG. 1C comprises sixteen independently controllable cells 12 arranged in a four cell by four cell square array, each cell 12 configured to produce a specified proton concentration in an associated volume of an environment including an electrolyte held in container 14. The volumes associated with each cell 12 are the volume of environment held in container 14 proximal to that cell 12. As there are no barriers or other impediments between the volumes, device 10 is configured to allow substantially uninhibited movement of ions between neighboring volumes. Device 22 may be used to produce many different proton concentration topographies, including proton concentration topography vii depicted in FIG. 1B.

Method for Producing a Specified Proton Concentration in an Environment

Implementation of embodiments of the invention for producing a proton concentration topography as described above are contingent on producing a specified proton concentration in an environment, for example in a volume of an environment associated with a cell as described above.

Any suitable method for producing a specified proton concentration in an environment may be used. That said, some embodiments of the invention provide a method for producing a specified proton concentration in an environment including an electrolyte, comprising: a) providing an environment including an electrolyte; b) contacting a working electrode and a counter electrode with the environment so that: a first side of the working electrode faces the counter electrode to define a electrolysis volume of the environment between the working electrode and the counter electrode, and a second side of the working electrode faces a second volume of the environment; c) specifying a desired proton concentration; d) passing a current between the working electrode and the counter electrode so as to electrolyze components of the environment to generate electrolysis products in the electrolysis volume; and e) transferring at least some electrolysis products to the second volume, thereby producing a proton concentration in the second volume of the environment, wherein the current is such that the proton concentration produced in the second volume is the specified proton concentration.

In some embodiments, the working electrode is permeable to the passage of the electrolysis products therethrough (e.g., is made of mesh) and the transferring of electrolysis products includes allowing the electrolysis products generated in the electrolysis volume to pass through the working electrode into the second volume, thereby producing the proton concentration in the second volume.

In some embodiments, the working electrode is an anode and the counter electrode is a cathode.

In some embodiments, the working electrode is a cathode and the counter electrode is an anode.

In some embodiments the method further comprises: f) monitoring (continuously or periodically) the proton concentration produced in the second volume of the environment; and g) if necessary, adjusting the current passing between the working electrode and the counter electrode so as to maintain the proton concentration produced in the second volume as the specified proton concentration.

In some embodiments, the method further comprises: subsequent to d, specifying a desired proton concentration different than a previously specified proton concentration; and passing a current between the working electrode and the counter electrode, thereby producing a proton concentration in the second volume of the environment, wherein the current is such that the proton concentration produced in the second volume is the different specified proton concentration.

In some embodiments, the method further comprises: changing (stepwise or continuously) the current as a function time, thereby changing the proton concentration produced in the second volume as a function of time.

Device for Producing a Specified Proton Concentration in an Environment

Any suitable device for producing a specified proton concentration in an environment may be used in implementing the teachings of the invention.

That said, some embodiments provide a device that may be used to implement a method for producing a specified proton concentration in an environment including an electrolyte, comprising: a) a working electrode; and b) a counter electrode, the working electrode and the counter electrode arranged so that: a first side of the working electrode faces the counter electrode to define a electrolysis volume between the working electrode and the counter electrode, and a second side of the working electrode faces a second volume of a container, the container configured to contain an environment including an electrolyte, wherein the electrolysis volume is in fluid communication with the second volume of the container.

In some embodiments, the working electrode is permeable to the passage of electrolysis products therethrough (e.g., is made of mesh) to allow electrolysis products generated in the electrolysis volume to pass through the working electrode into the second volume.

In some embodiments, the device further comprises an environment including an electrolyte contained within the container, filling the electrolysis volume and contacting the working electrode and the counter electrode.

In some embodiments, the container has dimensions of the order of the counter electrode and of the second volume, and the container is at least partially physically defined by a barrier impermeable to the passage of ions.

In some embodiments, the container has dimensions substantially larger than the dimensions of the second volume.

In some embodiments, the device is configured to allow establishment of an electrical circuit between the working electrode and the counter electrode when an environment including an electrolyte fills the container and the electrolysis volume.

In some embodiments, the device further comprises a controller configured to allow variation of the magnitude of an electrical current passing through an established electrical circuit.

In some embodiments, the device further comprises a proton concentration sensor functionally associated with the cell and with the controller, the proton concentration sensor configured to determine the value of a proton concentration in the second volume and to report the value of the proton concentration to the controller, and the controller is further configured to change a magnitude of an electrical current passing through an established electrical circuit in response to the reported value. In some embodiments, comprises a proton concentration sensor is used as a component of a feedback circuit to provide better control of a cell.

In some embodiments, the device further comprises a controller input component functionally associated with the controller, configured to allow a user to input a desired value that influences the magnitude of an electrical current passing through an established electrical circuit.

In some embodiments, the controller is configured to vary the electrical current passing through an established electrical circuit as a function of time, allowing a proton concentration generated in the second volume to be changed as a function of time.

Figure 2A:
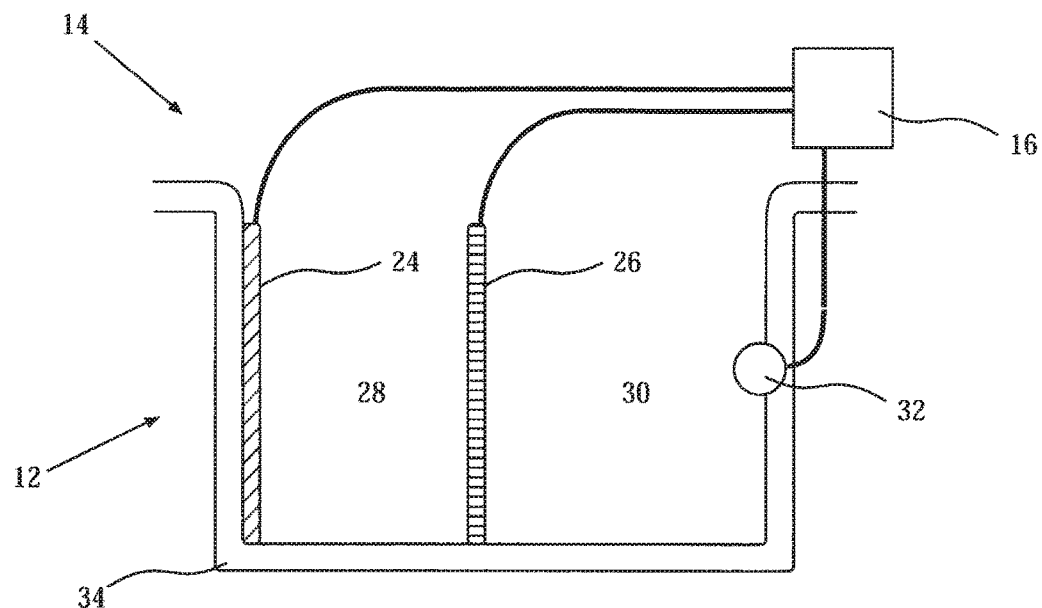
FIG. 2A schematically depicts, in side cross section, a device for producing a specified proton concentration.

In FIG. 2A, a device for producing a specified proton concentration in an environment, cell 12 is schematically depicted in side cross-section. Cell 12 comprises a counter electrode 24, a working electrode 26 (a mesh permeable to the passage of ions), an electrolysis volume 28 (the volume between working electrode 26 and counter electrode 24), a second volume 30 on the opposite side of working electrode 26 and a proton concentration sensor 32 in second volume 30, all contained within the volume defined by container 14. Electrodes 24 and 26 are functionally associated with controller 16, which is configured to control the magnitude of a current passing between electrodes 24 and 26 when an environment including an electrolyte is contained within container 14 and in contact with electrodes 24 and 26.

For use, an environment including an electrolyte is added to container 14 filling electrolysis volume 28 and second volume 30 and establishing an electrical circuit including electrodes 24 and 26. Controller 16 passes an electrical current through the established circuit between electrodes 24 and 26. Electrolysis occurs in electrolysis volume 28, electrolyzing water to generate electrolysis products such as protons and hydroxyl anions. The protons migrate to the cathode while the hydroxyl anions migrate to the anode, changing the proton concentration in the vicinity of the electrodes.

Ions in the vicinity of working electrode 26 pass through working electrode into second volume 30, changing the proton concentration in second volume 30 to be substantially equal to that near working electrode 26.

Proton concentration sensor 32 determines the value of a proton concentration in second volume 30 and reports the value of the proton concentration to controller 16 which then, if necessary, changes the magnitude of the electrical current in response to the reported value in order to produce a desired proton concentration in second volume 30, as input to controller 16 by a user through the controller input component of controller 16.

Figure 2B:
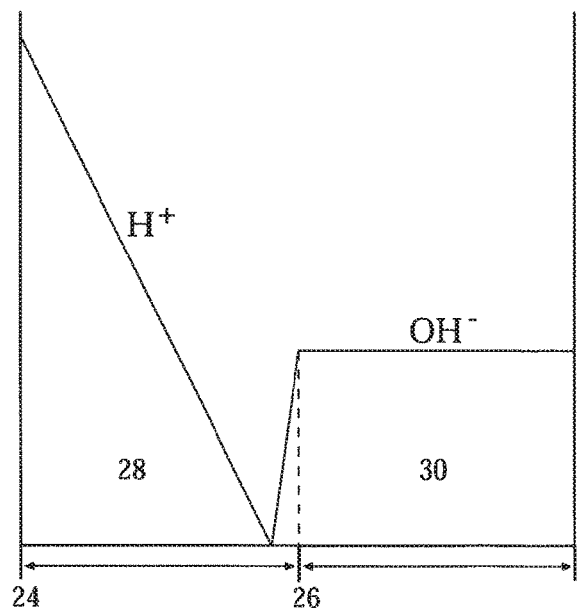
FIG. 2B is a graph qualitatively showing the concentration of products of electrolysis in the device of FIG. 2A.

In FIG. 2B is shown a graph qualitatively depicting the concentration of protons and hydroxyl anions in device 22 of FIG. 2A when activated so that working electrode 26 is an anode and counter electrode 24 is a cathode. It is seen that the proton concentration monotonously decreases through electrolysis volume 28 from a maximum near counter electrode 24. In the proximity of working electrode 26 as well as in second volume 30 there is a high concentration of hydroxyl anions and consequently a low concentration of protons. It is seen that the concentration of hydroxyl anions in all of second volume 30 is the same and substantially the same as the concentration near working electrode 26.

Methods and Devices for Isoelectric Focusing

As discussed above, isoelectric focusing is based on providing a suitable proton concentration topography, for example, a topography where the concentration of protons changes monotonously in a given direction, and application of a potential difference parallel to the direction. In the art, isoelectric focusing is performed in proton concentration gradients immobilized in gels.

The teachings of the invention may be applied to perform isoelectric focusing, where the proton concentration topography is not-immobilized.

Some embodiments of the invention provide a method of analyzing an analyte using isoelectric focusing, comprising: a) placing an analyte suitable for analysis by isoelectric focusing in an environment including an electrolyte; b) producing a non-immobilized proton concentration topography in the environment; c) applying an electric potential difference to the environment; and d) observing locations of components of the analyte in the environment in relation to the proton concentration topography and the electric potential difference, thereby analyzing the analyte using isoelectric focusing.

Observing the locations of the components is by any suitable method and generally depends on the nature of the analytes. For example, in some embodiments, fluorescent analytes (e.g., proteins) are observed with the help of a fluorescence detector.

In some embodiments, the environment is a fluid. This is in contrast to known methods of isoelectric focusing where the environment in which the proton concentration topography needed for isoelectric focusing is a gel. The use of a fluid allows for quicker isoelectric focusing as the components of the analytes migrate to the isoelectric point more quickly, is cheaper as no expensive and sensitive gels need to be manipulated, and allows high-throughput analysis as a single device may be used to serially analyze analytes automatically: after analysis of an analyte is completed, the fluid is drained, the device washed and fresh fluid introduced.

In some embodiments, the proton concentration topography is mutable. In some embodiments, the method further comprises: e) subsequent to d, changing the mutable proton concentration topography to a second non-immobilized proton concentration topography; and f) observing the location of components of the analyte in the environment in relation to the second proton concentration topography and the electric potential. Such embodiments allow performance of multiple analyses of the same sample. For example, a first proton concentration topography covering a broad range of proton concentrations is used to provide a rough indication of the isoelectric points of the components of the analyte (i.e., at "low resolution"). Subsequent proton concentration topographies are produced, each such topography including a limited range of proton concentrations spanning the proton concentrations necessary to determine the isoelectric point of a specific component of the analyte (i.e., at "high resolution"). In such a way, the isoelectric point of each component of an analyte may be determined with great accuracy.

In some embodiments, the method further comprises: subsequent to d, while observing, intermittently or continuously, locations of components of the analyte in the environment, changing the proton concentration topography as a function of time. Such embodiments are useful for "scanning" an unknown analyte to determine a limited range of isoelectric points before performing a more exacting analysis.

In some embodiments, devices for isoelectric focusing according to the invention are devices for producing a proton concentration topography, for example such as described above, but provided with an anode and a cathode for applying the isoelectric focusing field. When necessary, ion concentrations and the like may be determined using commercially available components, for example based on ion sensitive field-effect transistors technology.

As noted above, some embodiments of the invention are directed to methods and devices for generating a proton concentration topography for use in isoelectric focusing and related analyte separation methods.

Figure 3A:
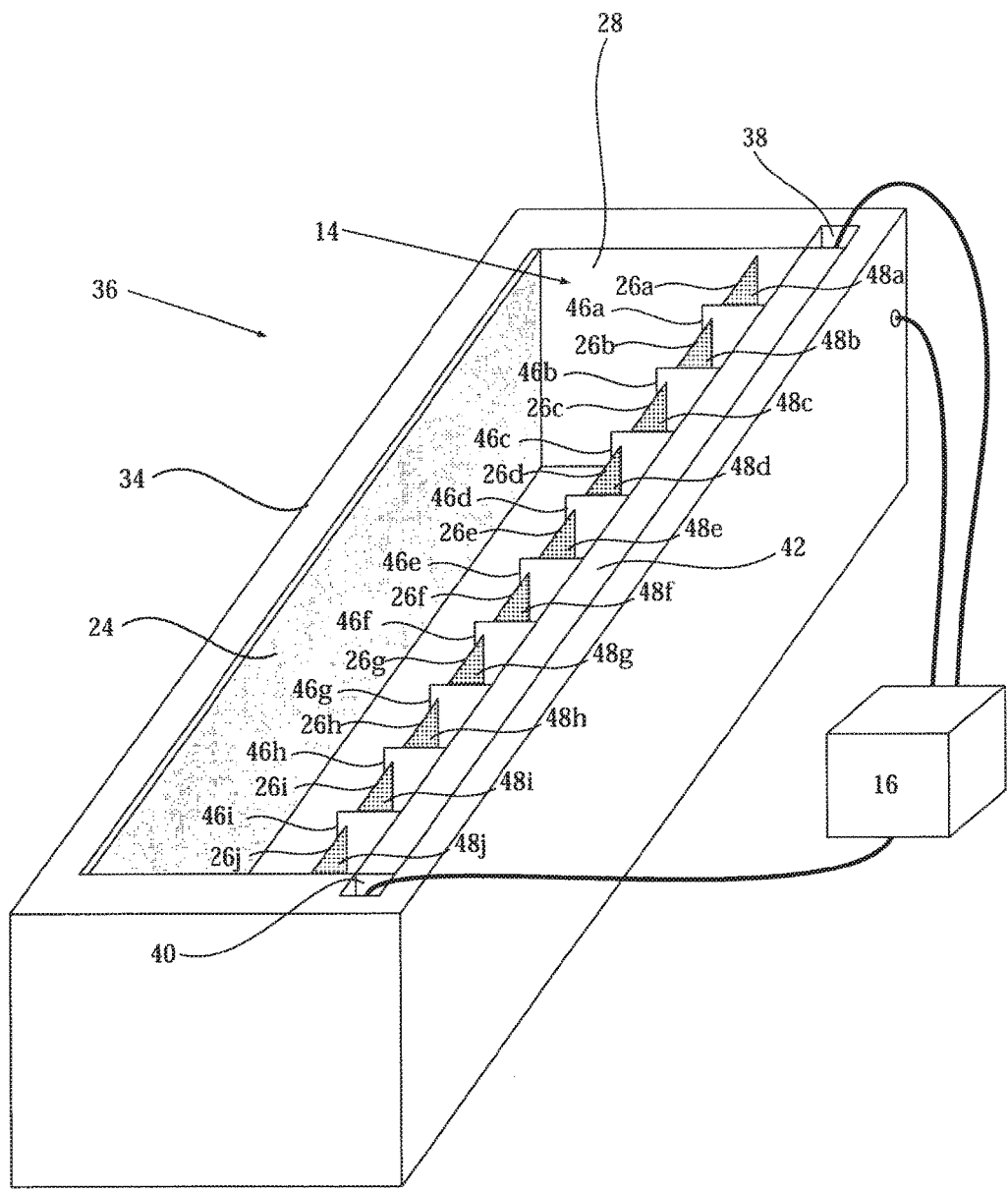
FIGS. 3A-3C schematically depict a device for producing a one-dimensional proton concentration topography suitable for use in isoelectric focusing.

An embodiment of a device configured producing a proton concentration topography and useful for isoelectric focusing in accordance with the teachings of the invention, device 36, is depicted in FIGS. 3A (perspective), 3B (side view) and 3C (top view).

Casing 34, substantially a non-conductive rectangular box of transparent polycarbonate with an open top, about 5 cm long, 0.5 cm wide, 0.5 cm deep contains other components of device 36. The volume defined by casing 34 is considered to be a container 14.

On one side of casing 34 is found a substantially standard electrophoresis assembly comprising an isoelectric focusing anode 38, an isoelectric focusing cathode 40 and an electrophoresis gel 42 (e.g., neutral uncharged polyacrylamide hydrogel available from Bio-Rad Haifa, Ltd., Haifa, Israel). By functionally associating anode 38 and cathode 40 with a standard electrophoresis power source, electrophoresis may be performed in the usual way in gel 42.

One face of gel 42 contacts a wall of casing 34. Contacting the opposing face of gel 42 is a membrane 44 (e.g., a hydrophilic polyvinylidene fluoride (PVDF) membrane with 5 micrometer pores available, for example as Durapore (SVLP04700) from Millipore, Inc. Billerica, Mass., USA) that physically supports gel 42 and allows substantially free passage of ions and water molecules between gel 42 and the rest of the volume of container 14.

Container 14 contains components of an array of a plurality (ten) independently controllable cells, similar to cell 12 depicted in FIG. 2A. Each cell of the array of cells is configured to produce a specified proton concentration in an associated volume of gel 42. Taken collectively, cells of the array of cells are configured for producing a one-dimensional (linear) proton concentration topography in gel 42 in accordance with aspects of the invention.

The array of cells includes a single counter electrode 24 (platinum sheet) opposing ten individually controllable working electrodes 26a-26j (platinum mesh, made of 0.1 mm thick wires with 0.1 mm gaps), each working electrode 26 separated from neighboring working electrodes 26 by an electrode separator 46a-46i (0.1 mm glass walls). Working electrodes 26a-26j are placed about 0.5 mm from membrane 44 and about 2 mm from counter electrode 24 by.

The volume defined between working electrodes 26 and counter electrode 24 is an electrolysis volume 28.

The volume defined by a working electrode 26, one or two bordering electrode separators 46 and membrane 44 is a proton reservoir volume 48a-48j, on the bottom of which is embedded a proton concentration sensor 32a-32j (e.g., Orion 9863BN, Thermo Fisher Scientific Inc., Waltham, Mass., USA) and a magnetic stirrer 50a-50j.

For use, electrolysis volume 28 and proton reservoir volumes 48a-48j are filled with an electrolyte solution (e.g., 0.1 M $Na_2SO_4$ in water).

Isoelectric focusing anode 38, isoelectric focusing cathode 40, counter electrode 24, working electrodes 26, proton concentration sensors 32 and stirrers 50 are all functionally associated with a controller 16 (e.g., an appropriately configured microprocessor or digital computer with necessary peripheral accessories).

Stirrers 50 and proton concentration sensors 32 are activated.

Controller 16 activates each cell so that a selected current, typically between 0 and about 1 $mA\ cm^{-2}$ (depending on the desired proton concentration) is independently established between counter electrode 24 and each working electrode 26a-26j so that a voltage of between 0 and about 5V exists between counter electrode 24 and each working electrode 26a-26j.

As the system stabilizes, a proton concentration gradient (substantially as depicted in FIG. 2B) is generated in the environment including an electrolyte held in electrolysis volume 28 between counter electrode 24 and each working electrodes 26a-26j. As discussed with reference to FIG. 2B, in each proton reservoir volume 48a-48j, a single stable and uniform proton concentration is maintained due to the small volume of a proton reservoir volume 48 as well as due to the action of stirrers 50. The proton concentration in each proton reservoir volume 48 influences the proton concentration in gel 42 through membrane 44 so that the proton concentration in a given proton reservoir volume 48 is the same in a volume of gel 42 immediately adjacent to that proton reservoir volume 48.

With reference to proton concentration sensors 32, the current passing between counter electrode 24 and each working electrode 26a-26j is changed until a desired proton concentration (as specified by controller 16) is produced and detected in an associated proton reservoir volume 48. As the current passing between counter electrode 24 and each working electrode 26a-26j is independently controllable, the proton concentration in each proton reservoir volume 48 and consequently in the adjacent volume of gel 42 is separately controllable. In such a way, a desired specified proton concentration topography is produced in gel 42, where each cell produces a specified proton concentration in a volume of gel 42 associated with that cell.

A mixture of one or more analytes for separation by isoelectric focusing is loaded onto gel 42 and a potential (e.g., 700 V) is supplied between isoelectric focusing anode 38 and isoelectric focusing cathode 40. The proton concentration topography inside gel 42 causes separation of the individual analytes in the mixture according to the isoelectric points. The locations of the individual analytes are observed and analyzed in the usual way. Once the mixture of analytes has been separated and analyzed at a first proton concentration topography, the potential on working electrodes 26 is optionally changed to generate a different proton concentration topography in order to have a different isoelectric separation which is also observed and analyzed in the usual way.

For example, in an embodiments a first proton concentration topography is specified to have a proton concentration having pH 5.0 in the volume of gel 42 associated with working electrode 26a, the proton concentration decreasing monotonously and linearly to a proton concentration having a pH 8.0 in the volume of gel 42 associated with working electrode 26j, while a second proton concentration topography is specified to have a proton concentration having pH 5.2 in the volume of gel 42 associated with working electrode 26a, the proton concentration decreasing monotonously and linearly to a proton concentration having a pH 5.9 in the volume of gel 42 associated with working electrode 26j.

For example, in an embodiments a first proton concentration topography is specified to have a proton concentration having pH 5.0 in the volume of gel 42 associated with working electrode 26a, the proton concentration decreasing monotonously and linearly to a proton concentration having a pH 6.0 in the volume of gel 42 associated with working electrode 26j, while a second proton concentration topography is specified to have a proton concentration having pH 5.8 in the volume of gel 42 associated with working electrode 26a, the proton concentration decreasing monotonously and linearly to a proton concentration having a pH 7.0 in the volume of gel 42 associated with working electrode 26j.

In the specific examples described hereinabove, in the direction through gel 42 from proximity with working electrode 26a to proximity with working electrode 26j, the proton concentration monotonously decreases. As is clear to one skilled in the art, the change in proton concentration in a direction through gel 42 may be substantially any desired function, monotonous or not.

Figure 4A:
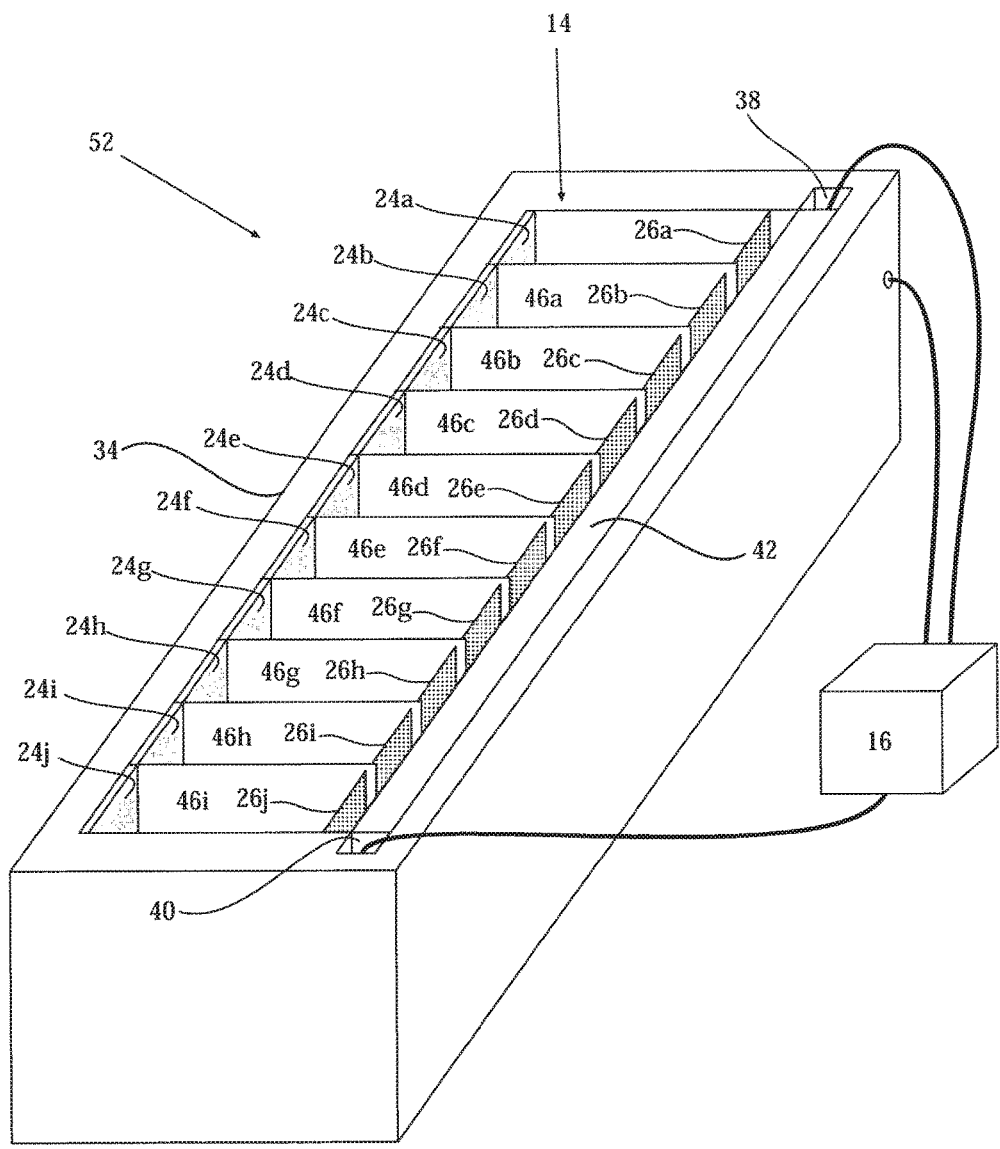
FIGS. 4A-4C schematically depict a device for producing a one-dimensional proton concentration topography suitable for use in isoelectric focusing.
Figure 4B:
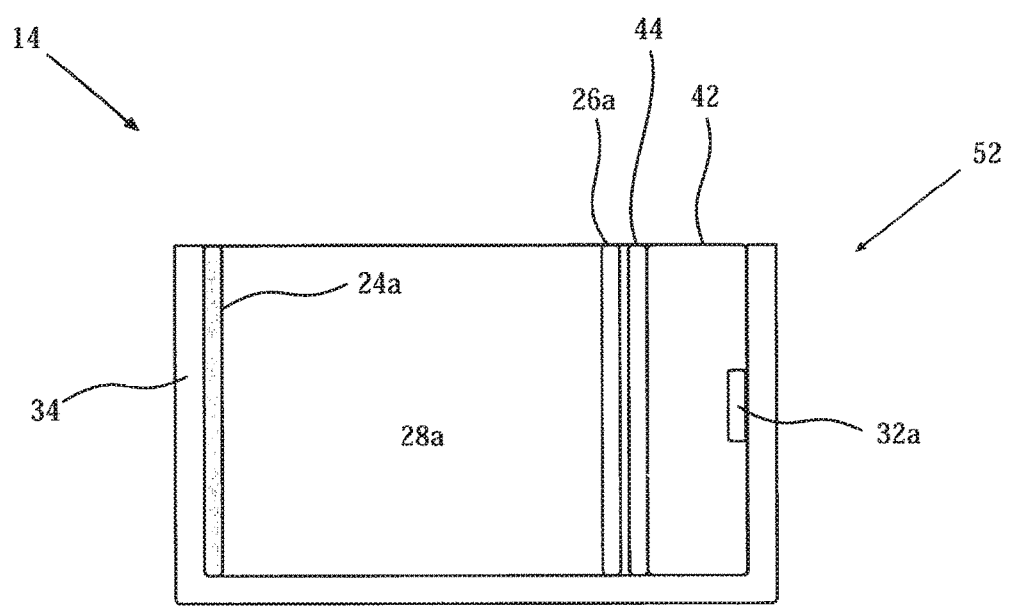
Figure 4C:
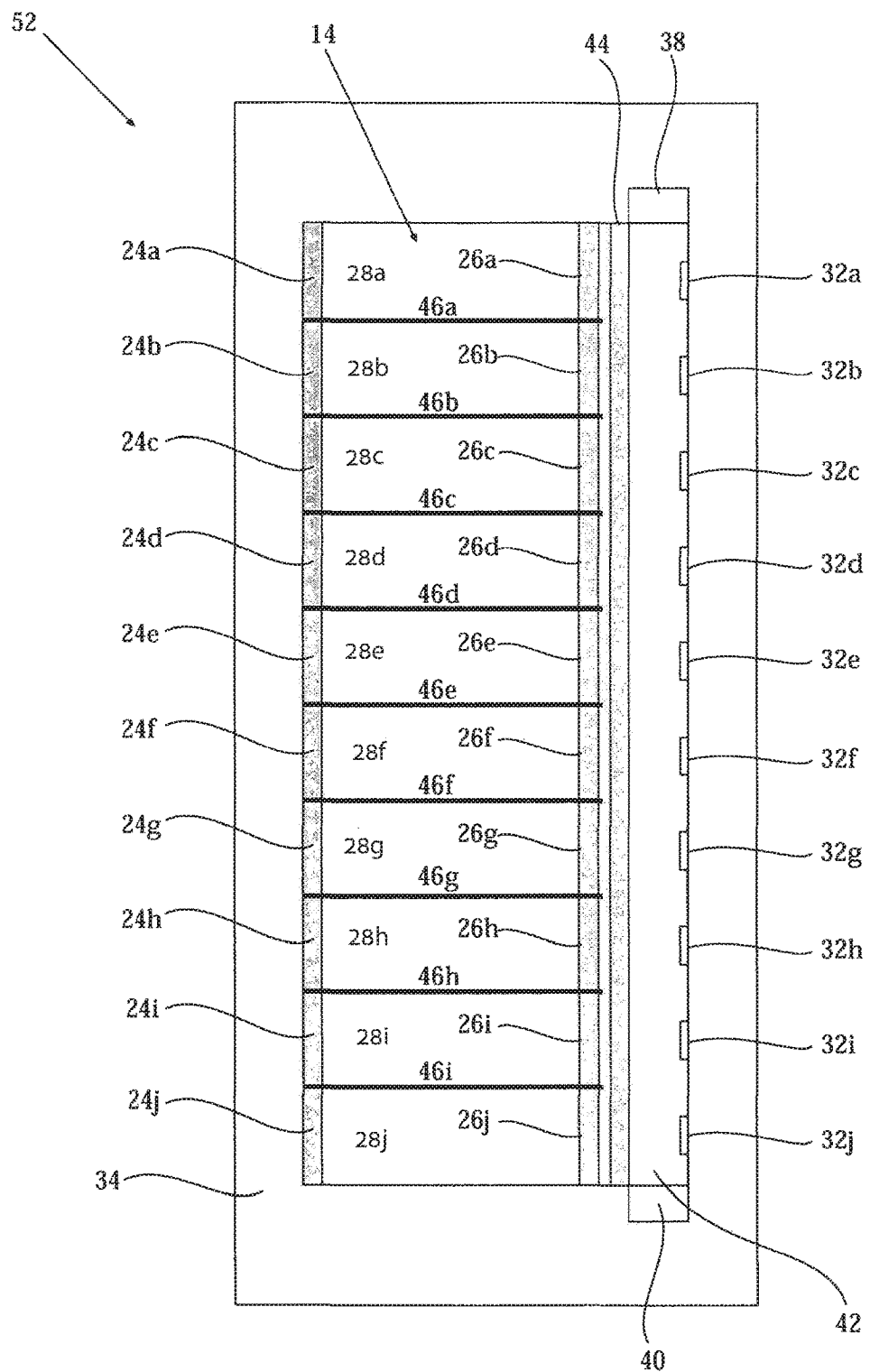

An additional embodiment of a device configured for producing a proton concentration topography and useful for isoelectric focusing in accordance with the teachings of the invention, a device 52, is depicted in FIGS. 4A (perspective view), 4B (side view) and 4C (top view).

Device 52 substantially resembles device 36 but includes a number of notable differences. One difference is that there is not one counter electrode 24 that functions opposite a plurality of working electrodes 26a-26j but rather a plurality of independent counter electrodes 24a-24j, each functionally associated with a respective working electrode 26a-26j. An additional difference is that electrode separators 46a-46i separate neighboring counter electrodes 24a-24j as well as neighboring working electrodes 26a-26j, thereby defining a plurality of physically discrete electrolysis volumes 28a-28j.

Additionally, proton concentration sensors 32 are embedded inside a gel 42 on a wall of a casing 34 opposite a respective counter electrode 24 so as to measure the actual proton concentration of a volume associated with a working electrode 26 inside gel 42. Further, device 52 is substantially devoid of proton reservoir volumes 48. Rather, the distance between working electrodes 26 and a membrane 44 is very small, approximately only 0.1 mm.

Figure 5A:
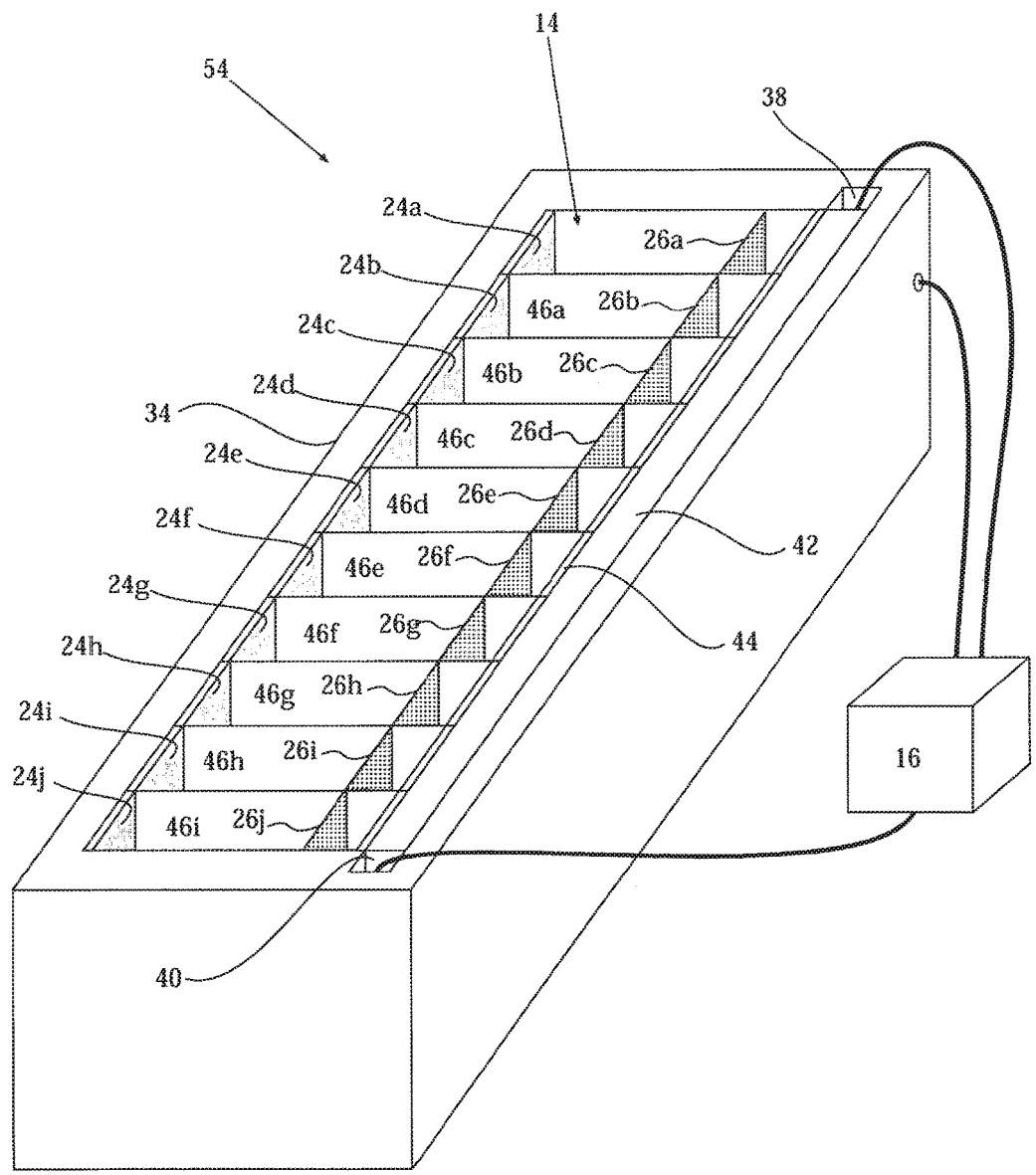
FIGS. 5A-5C schematically depict a device for producing a one-dimensional proton concentration topography configured for use in isoelectric focusing.

An additional embodiment of a device configured for producing a proton concentration topography and useful for isoelectric focusing in accordance with the teachings of the invention, a device 54, is depicted in FIGS. 5A (perspective view), 5B (side view) and 5C (top view).

Figure 5B:
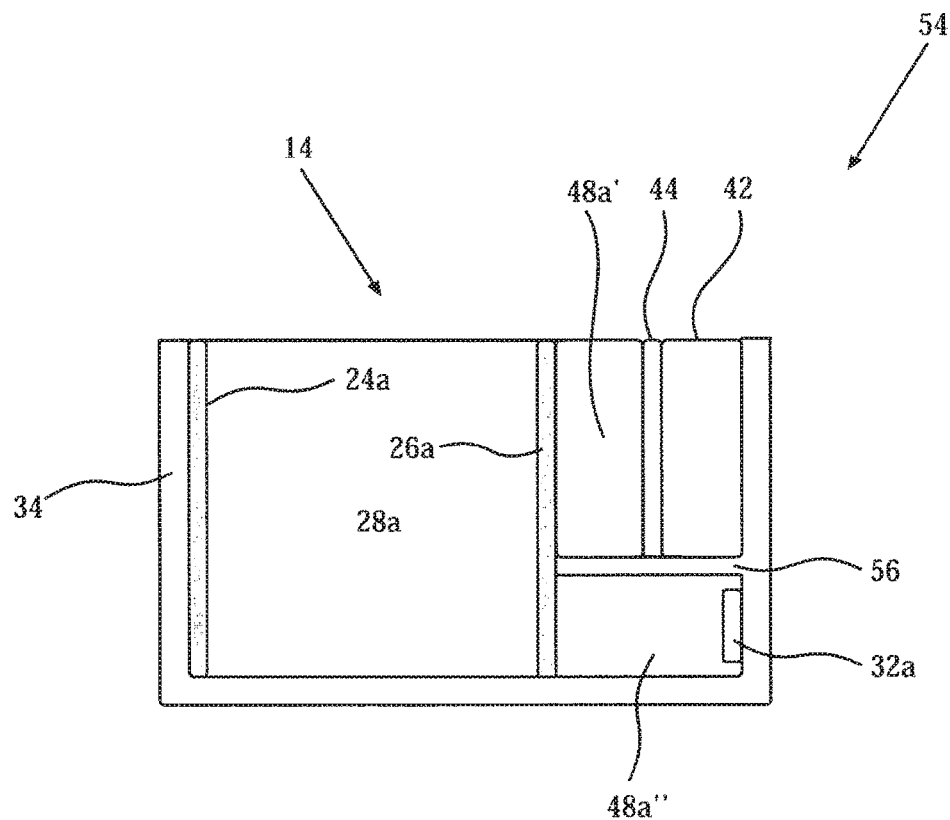
Figure 5C:
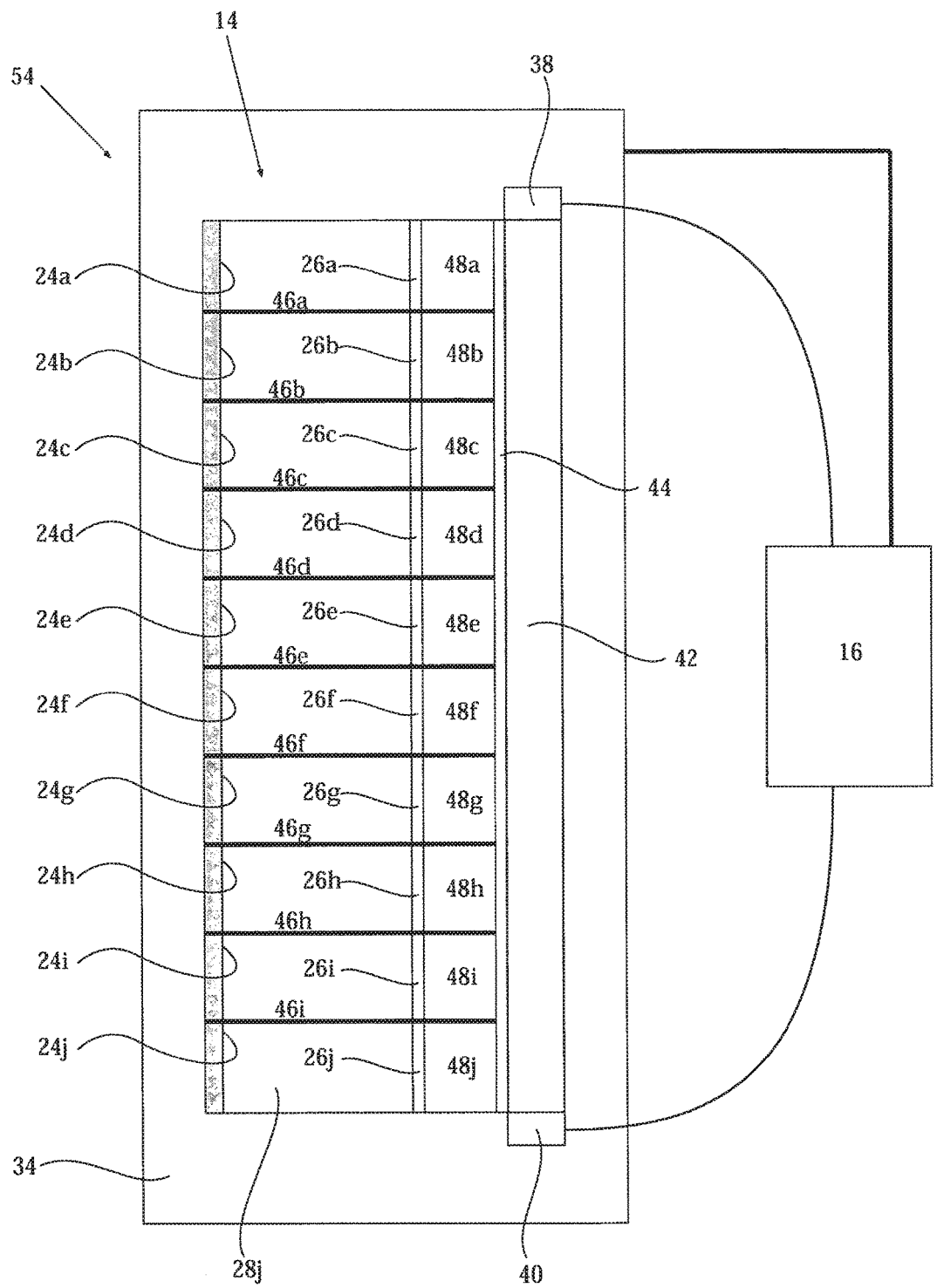

Device 54 substantially resembles devices 36 and 52 but includes a number of notable differences, including that device 54 is configured so that proton concentration sensors 32 are isolated from the influence of the electric field generated by isoelectric focusing anode 38 and cathode 40. Each proton reservoir volume 48 is divided into two parts, as seen in FIG. 5B, a first part 48' (in FIG. 5B, 48a' is depicted) and a second part 48" (in FIG. 5B, 48a" is depicted).

A first part of a proton reservoir volume 48, such as 48a', is defined by a working electrode 26, one or two bordering electrode separators 46 and membrane 44 so that protons and water molecules can pass substantially uninhibited between first part 48' and gel 42.

A second part of a proton reservoir volume 48, such as 48a", is defined by a working electrode 26 and one or two bordering electrode separators 46. Second part 48" is separated from first part 48' and from gel 42 by an insulating partition 56, for example of polycarbonate, so that movement of protons between second part 48" and gel 42 is inhibited. Proton concentration sensors 32 (in FIG. 5B, 32a is depicted) are contained within second part 48" of a volume 48. In such a way, proton concentration sensors 32 are isolated from the electric field between isoelectric focusing anode 38 and cathode 40.

Figure 6A:
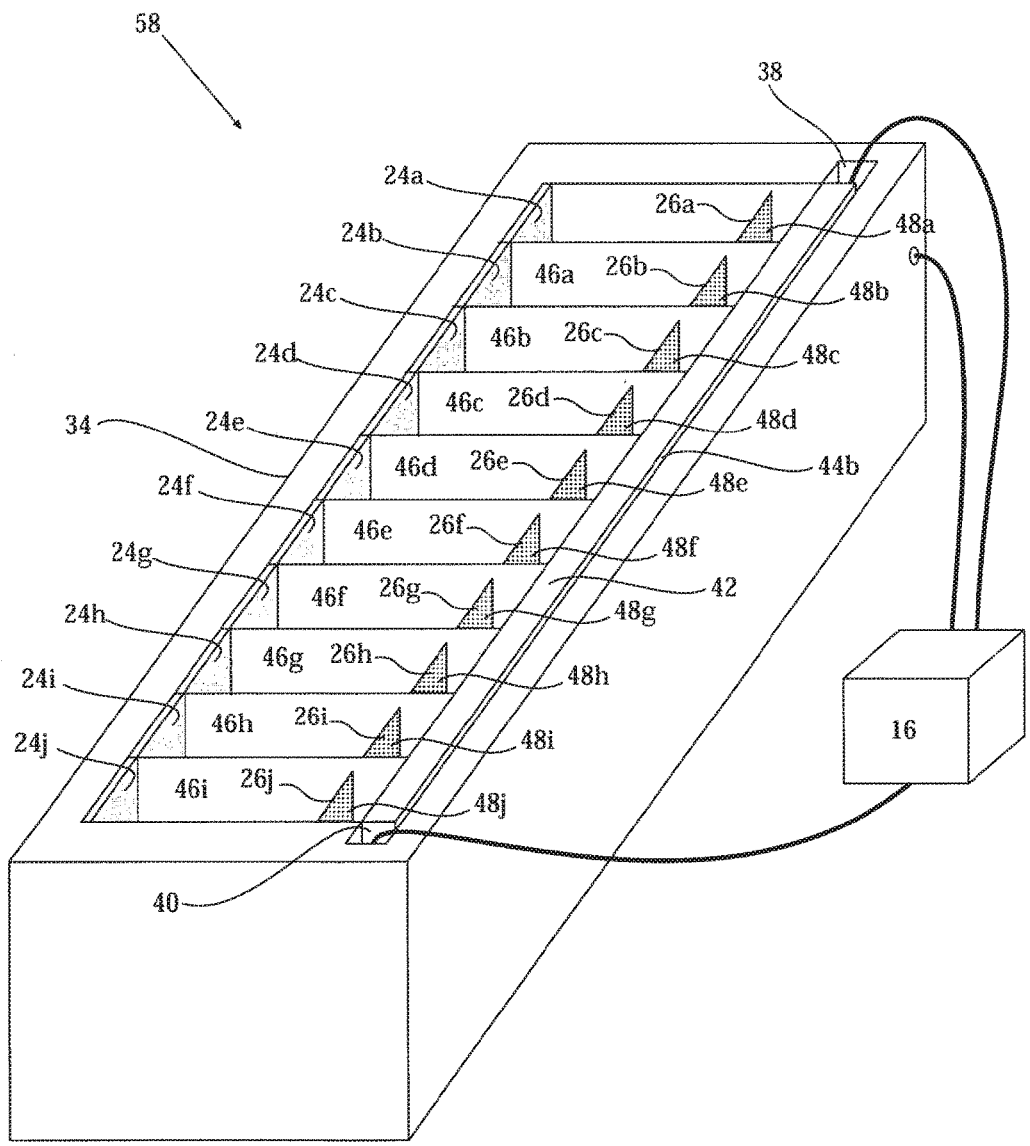
FIGS. 6A-6B schematically depict a device for producing a one-dimensional proton concentration topography configured for use in isoelectric focusing.
Figure 6B:
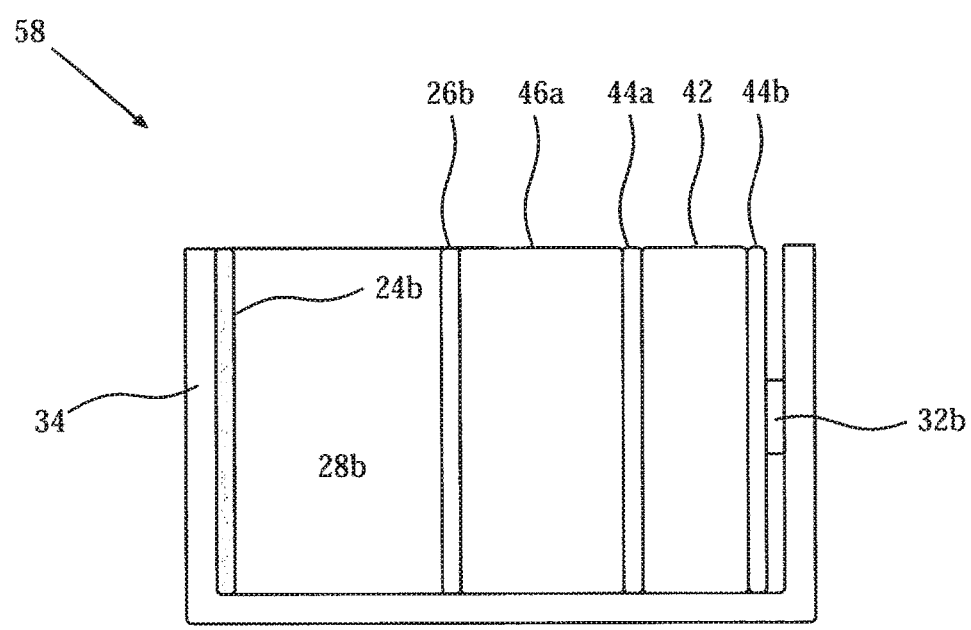

An additional embodiment of a device configured for producing a proton concentration topography and useful for isoelectric focusing in accordance with the teachings of the invention, device 58, is depicted in FIGS. 6A (perspective view) and 6B (side view).

Device 58 substantially resembles devices 36, 52 and 54 but includes a number of notable differences. Like in device 36, device 58 includes proton reservoir volume 48a-48j, defined by a working electrode 26, one or two bordering electrode separators 46 and a proton-permeable membrane 44a intimately associated with gel 42. Like in device 54, proton concentration sensors 32 are positioned on a wall of a casing 34 opposite a counter electrode 24, separated from direct contact with a gel 42 by a proton-permeable membrane 44b. However, unlike in device 54, in device 58 proton concentration sensors 32 are not embedded in gel 42 but rather contact a surface thereof.

Figure 9A:
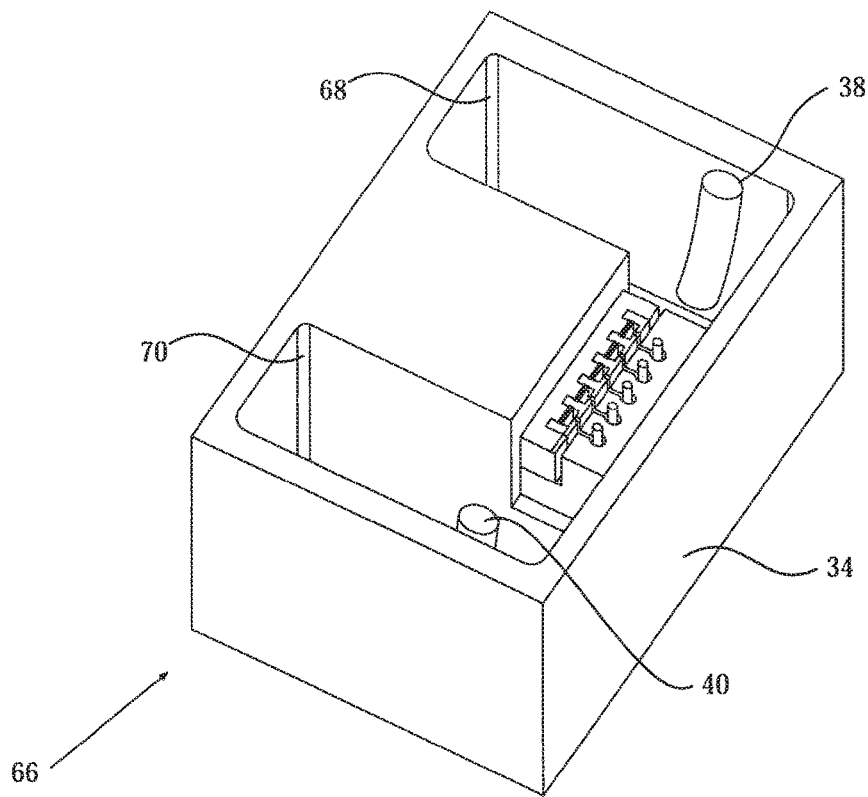
FIGS. 9A-9B schematically depict an embodiment of a device for producing a one-dimensional proton concentration topography configured for use in isoelectric focusing.

An additional embodiment of a device configured for producing a proton concentration topography and useful for isoelectric focusing in accordance with the teachings of the invention, device 66, is depicted in FIGS. 9A (perspective view) and 9B (top detailed view). Device 66 substantially resembles devices 36, 52, 54 and 58 but includes a number of notable differences.

Device 66 includes an array of five independently controllable cells 12a-12e substantially similar to cell 12 depicted in FIG. 2A. Each cell of the array of cells is configured to produce a specified proton concentration in an associated volume of an environment including an electrolyte held in proton concentration topography channel 72. Taken collectively, cells 12 of the array of cells are configured for producing a one-dimensional (linear) proton concentration topography in channel 72.

Device 66 is provided with a large anode bath 68 in which isoelectric focusing anode 38 is immersed and a large cathode bath 70 in which isoelectric focusing cathode 40 is immersed.

In device 66, components of each cell 12 are isolated from proton concentration topography channel 72 in separate volumes of container 14 to protect the components from damage from the electric field generated between anode 38 and cathode 40. Counter electrode 24 and working electrode 26 are isolated in a volume (which also includes an electrolysis volume 28 and a proton reservoir volume 48), the volume in fluid communication with proton concentration topography channel 72 through a narrow conduit that constitutes a portion of a respective proton reservoir volume 48. The volume of an environment including an electrolyte that is found in proton concentration topography channel 72 in proximity to the opening of each conduit together with proton reservoir volume 48 comprises the volume associated with each cell 12 in which a specified proton concentration is produced. In proton concentration topography channel 72, between any two such volumes are found interface volumes having a proton concentration (and in some cases, a proton concentration gradient) related to the proton concentrations of the two neighboring volumes defining the interface volume.

Each proton concentration sensor 32 is isolated in a respective proton concentration sensor volume 74 from proton concentration topography channel 72 in fluid communication with proton concentration topography channel 72 through a narrow conduit. In some embodiments (not depicted) pumps (e.g., peristaltic pumps) or other suitable device provide fluid communication between a proton concentration sensor volume 74 and a respective proton reservoir volume 48 to ensure that the proper proton concentration is measured.

In devices 36, 52, 54 and 58, the environment including an electrolyte in which a specified proton concentration topography is produced comprises the electrolyte solution and gel 42. In devices 66, the environment including an electrolyte in which a specified proton concentration topography is produced comprises the electrolyte solution held in proton concentration topography channel 72.

In devices 36, 52, 54, 58 and 66, the container configured to contain the environment including the electrolyte comprises container 14, including the portion in which a gel 42 is held or the proton concentration topography channel 72 of device 66.

In devices 36, 52, 54 and 58, the individual independently controllable cells configured to produce a specified proton concentration in an associated volume of an environment including an electrolyte comprise counter electrode 24, electrolysis volume 28, a working electrode 26, a proton concentration sensor 32 and for devices 36, 54, 58 and 66, a proton reservoir volume 48.

In device 36, the electrolysis volumes of each cell are not physically separated and there is a single counter electrode 24 for all working electrodes 26a-26j. However, in embodiments where a potential is applied between an isoelectric focusing anode 38 and an isoelectric focusing cathode 40, it is often advantageous that each working electrode 26 is provided with a dedicated counter electrode 24 to reduce interference between neighboring cells. Consequently, in devices 36, 52, 54, 58 and 66, each cell includes an electrolysis volume 28 between a working electrode 26 and a respective counter electrode 24.

In devices 36, 54 and 58, the volume of environment associated with a cell in which a specified proton concentration is produced includes a proton reservoir volume 48 as well as the volumes of membrane(s) 44 and gel 42 located proximally to a respective proton reservoir volume 48. In devices 52, the volume of environment associated with a cell in which a specified proton concentration is produced includes a the volumes of membrane 44 and gel 42 located proximally to a respective working electrode 26.

In devices 36, 52, 54, 58 and 66, proton concentration sensors 32 measure proton concentrations produced by a cell (e.g., 12) and report the measured concentration to controller 16. This allows monitoring of the actually produced proton concentrations and, if necessary, adjustment of the current passing between a working electrode 26 and a counter electrode 24 to maintain the actually produced proton concentration as a specified proton concentration.

As described above, when a device 36, 52, 54, 58 and 66 is operating to produce a proton concentration topography, gel 42 or environment held in channel 72 is divided into a plurality of discrete volumes characterized by a specified proton concentration, each volume associated with and in proximity to a specific working electrode 26 and in the case of devices 36, 54, 58 and 66 a respective proton reservoir volume 48. In gel 42 and in channel 72, between any two such associated volumes (and close to electrode separators 46) are interface volumes having a proton concentration (and in some cases, a proton concentration gradient) related to the proton concentrations of the two neighboring volumes defining the interface volume.

In some embodiments, a device of the invention such as device 36, 52, 54, 58 or 66 is configured so that a produced proton concentration topography in a gel 42 or proton concentration topography channel 72 is mutable and a proton concentration topography may be changed as desired and/or varied with time.

In some such embodiments, a controller 16 is provided with a user interface that allows a user to provide instructions specifying a desired proton concentration produced by each cell or to specify a desired proton concentration topography, as needed. Upon receipt of user instructions, controller 16 changes (or maintains) the current passing between one or more counter electrodes 24 and respective working electrodes 26 so as to produce the desired proton concentration topography.

In some such embodiments, controller 16 is provided with a timer and instructions as how to change a produced proton concentration topography as a function of time. With reference to the timer, controller 16 changes (or maintains) the current passing between one or more counter electrodes 24 and respective working electrodes 26 in accordance with the instructions so as to change the produced proton concentration topography as a function of time. The change in current may be such that the change in proton concentration produced by a cell changes in a step-wise fashion (that is to say, is allowed to stabilize at a certain value and is maintained at that value for some time) or continuously.

In some embodiments, such as device 36, each proton reservoir volume 48 is provided with a dedicated stirrer 50. In some embodiments, a proton reservoir volume is devoid of an actual stirrer and a uniform proton concentration is achieved by diffusion of protons inside the proton reservoir volume.

Figure 9B:
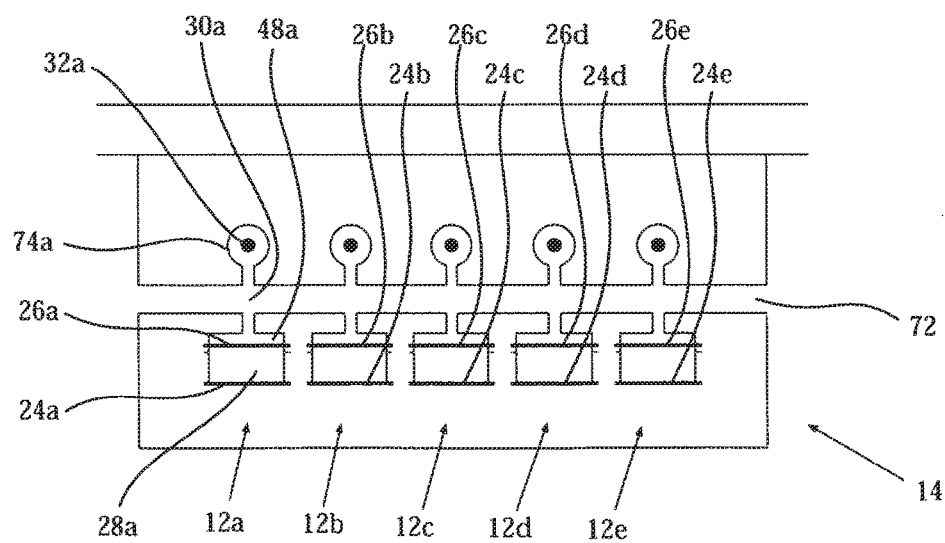

In some embodiments operation of a device such as a device 36, 52, 54, 58 or 66 may lead to the generation of heat, especially when a current passes between isoelectric focusing anode 38 and isoelectric focusing cathode 40. In some such embodiments, a device is provided with a cooling system, for instance comprising components to cool the environment including an electrolyte. In a typical example, a device such as device 66 depicted in FIG. 9 is provided with cooling elements in the walls of anode bath 68 and cathode bath 70.

In the embodiments discussed above, isoelectric focusing is performed in a portion of the environment that is gel 42 or in channel 72 in which a proton concentration topography is produced that is non-immobilized and is mutable. Some advantages include the ability to use cheaper gels with greater reproducibility and the possibility, discussed herein, to analyze the same sample of analyte using a number of different proton concentration topographies.

An embodiment demonstrating the utility of a mutable proton concentration gradient when performing isoelectric focusing is discussed with reference to FIGS. 10A-10F. In the embodiment, it is desired to resolve two proteins of interest having a similar electrophoretic mobilities but different isoelectric points (e.g., at pH 5.5 and at pH 6.5), the two proteins in a mixture together with three other proteins having different electrophoretic mobilities and unknown isoelectric points. Each of FIGS. 10A-10F schematically depicts the location of the five proteins of the mixture (each depicted as a horizontal strip) in gel 42, a standard electrophoresis/isoelectric focusing gel, in which a proton concentration topography is produced and across which an electrical field is applied between isoelectric focusing anode 38 and isoelectric focusing cathode 40. A characteristic of the embodiment is that electrophoretic separation and isoelectric resolution are performed on parallel axes, and not perpendicular axes as known in the art.

A uniform proton concentration (pH 7) is produced throughout gel 42 and the mixture of proteins is loaded onto gel 42 in the usual way. A potential is applied between anode 38 and cathode 40.

In FIG. 10A, the individual proteins move at different rates move as a result of electrophoresis.

In FIG. 10B, the individual proteins have reached the maximal electrophoretic resolution with the "fastest" protein proximal to anode 38. It is seen that the two proteins of interest are close together.

In FIG. 10C, a complex proton concentration topography is produced to further resolve the proteins of interest. In a central region 76, the volume of gel 42 in which the two proteins of interest are found, the proton concentration monotonously decreases from pH 2 (on the side of anode 38) to pH 10 (on the side of cathode 40). From the end of central region 76 having pH 2 towards cathode 40, a cathode region 78 (a volume of gel 42 which includes two "unwanted" proteins) the proton concentration decreases monotonously from pH 2 to pH 10 proximal to cathode 40. From the end of central region 76 having pH 10 towards anode 38, an anode region 80 (a volume of gel 42 which includes an "unwanted" protein) the proton concentration increases monotonously from pH 10 to pH 2 proximal to anode 38.

In FIG. 10D, the three "unwanted" proteins in cathode region 78 and anode region 80 move each to a respective isoelectric point near the edges of gel 42 while the two proteins of interest in central region 76 are increasingly spatially resolved due to isoelectric focusing resulting from the proton concentration topography described with reference to FIG. 10C and the potential applied between anode 38 and cathode 40.

In FIG. 10E, central region 76 is lengthened, increasing the spatial resolution of the two proteins of interest. Cathode region 78 and Anode region 80 are made smaller, forcing the three "unwanted" proteins closer together, In FIG. 10F, the two proteins of interest in central region 76 are spatially well-resolved.

Thus, using a mutable proton concentration topography, the present invention provides a method of analyzing an analyte using isoelectric focusing, as described above, where the second non-immobilized proton concentration topography is chosen so that components of interest are spatially resolved to a greater extent than in the preceding non-immobilized proton concentration topography.

In some embodiments of the invention, isoelectric focusing is performed in an environment that is a fluid such as a liquid, e.g., an electrolyte solution, for example in channel 72 of device 66 or in some such environments gel 42 is removed and replaced with electrolyte solution. Some advantages in performing isoelectric focusing in a liquid is lower price, simpler replacement of the environment between analyses and no sieving effects that occur when large analyte molecules pass through channels inside gels. As discussed above, the use of a fluid environment also allows simple implementation of preparatory methods based on separation methods such as isoelectric focusing.

In the embodiments discussed above, the movement of ions between two neighboring volumes of the environment in gel 42 is substantially uninhibited, a configuration that is suitable for many uses, for example isoelectric focusing.

Figure 3B:
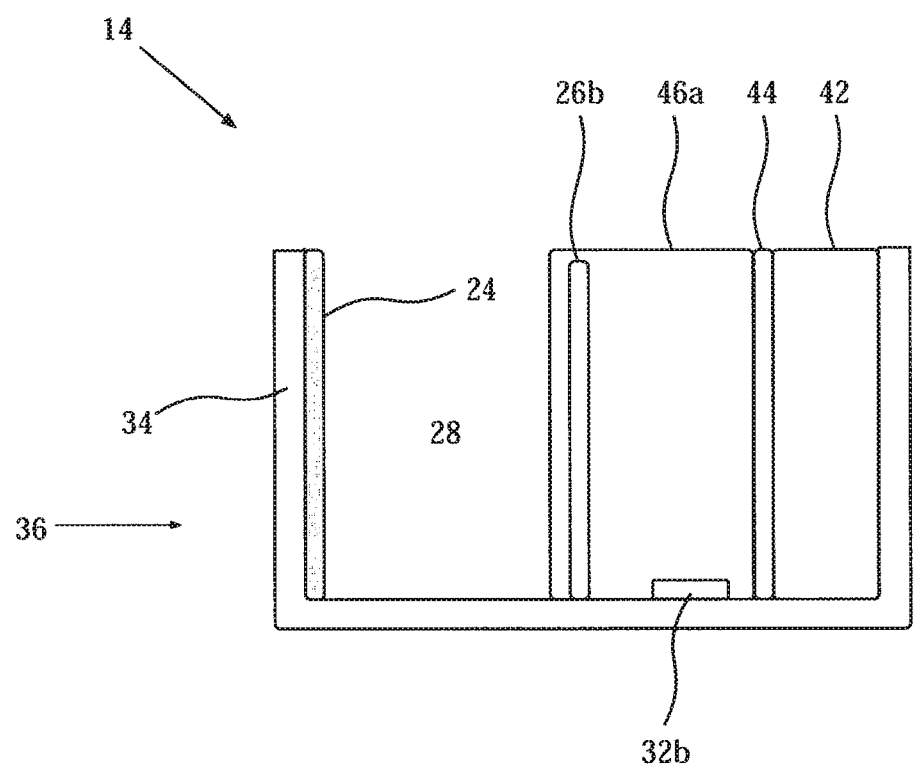
Figure 3C:
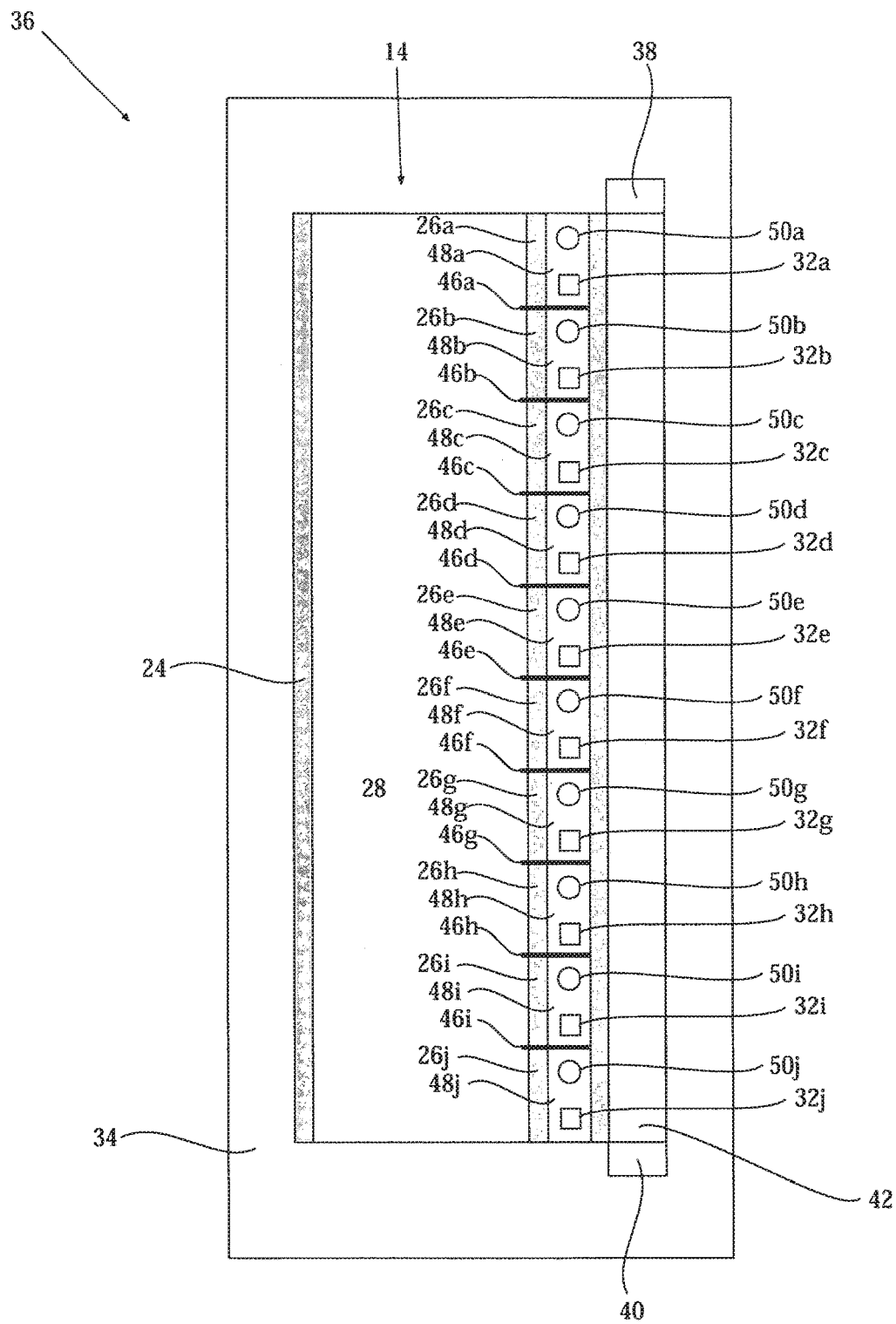

In some embodiments, the movement of ions between two neighboring volumes is inhibited. For example, one such embodiment where ion movement between neighboring volumes is substantially inhibited is similar to device 36 depicted in FIG. 3 where gel 42 is replaced with an insulating glass plate. In such an embodiment, the volume of the environment associated with an individual cell in which a specified proton concentration is produced includes only a respective proton reservoir volume 48. Such embodiments are useful, for example for the display of data.

For use, proton reservoir volumes 48 and electrolysis volume 28 are filled with an environment including an electrolyte and a pH sensitive indicator having an appearance that is dependent on the proton concentration in the environment, e.g. Yamada Universal pH indicator (see for example, Foster S F and Gruntfest in *J. Chem. Educ.* 1937, 14, 274). The individual cells are activated to produce specified proton concentrations in the respective proton reservoir volume 48. The indicator in proton reservoir volumes 48 adopts a color that is dependent on the produced proton concentration. The proton concentration in each proton reservoir volumes 48 is specified so that when the collective appearance of proton reservoir volumes 48 (that is of the produced proton concentration topography as made apparent by the pH indicator in the environment) constitutes a display of data for example an image.

As is clear to one skilled in the art, the display of data using a device similar to device 36 as described herein above having a one-dimensional array of cells producing a one-dimensional proton concentration topography is limited. Analogous devices having a two-dimensional array of cells to produce a two-dimensional proton concentration topography have greater utility, especially for the display of actual images.

Although an embodiment of the method and the device for displaying data were described where the movement of ions between two neighboring volumes is inhibited, in some embodiments for the display of data movement of ions between two neighboring volumes is substantially uninhibited.

Embodiments of the present invention are useful in fields other than isoelectric focusing and display of data, for example in microfluidics and lab-on-chip applications.

The teachings of the present invention may be implemented by a person having ordinary skill in the art upon perusal of the specification and figures using usual techniques and methods, for example as known in the field of microelectronics and microfluidics.

EXPERIMENTAL

Device for Producing a Specified Proton Concentration

Figure 7A:
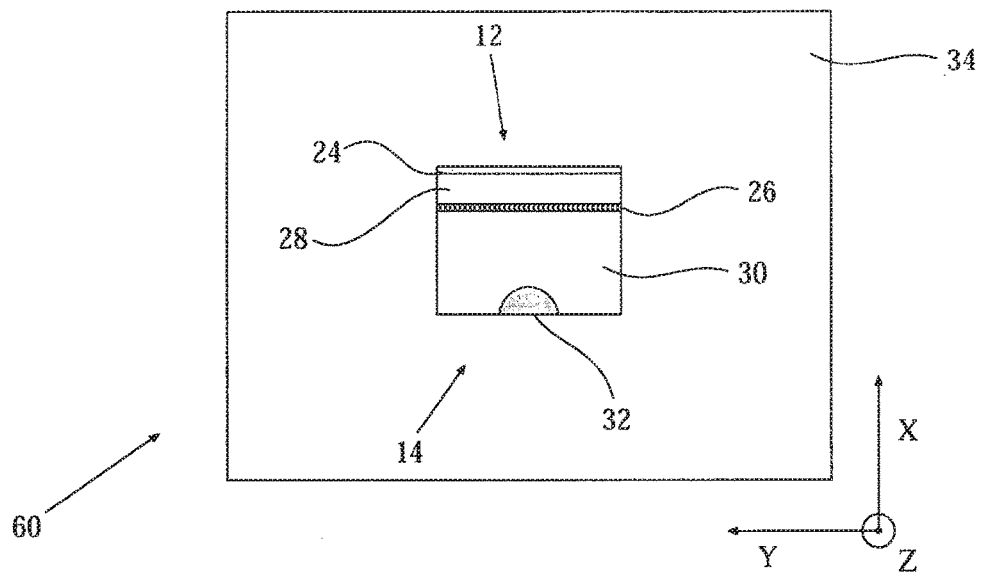
FIGS. 7A and 7B are schematic top views of devices for producing one-dimensional proton concentration topographies, the devices actually constructed and used for implementing the teachings of the invention.

An embodiment of a device for the production of a proton concentration in a liquid environment including an electrolyte, device 60 was made and used in accordance with the teachings of the invention to produce a specified proton concentration. Device 60 is schematically depicted in FIG. 7A in top view.

Casing 34 of device 60 is a block of polymethyl(methacrylate) (Perspex®) 4 cm long (y dimension), 3 cm wide (x dimension) and 2 cm high (z dimension) in which a container 14 was hollowed to accommodate a cell 12 for producing a specified proton concentration in an environment including an electrolyte, cell 12 being 1 cm long (y dimension), 0.6 cm wide (x dimension) and 1 cm deep (z dimension). Counter electrode 24 of 0.1 mm thick platinum mesh was placed along a wall of cell 12. Working electrode 26 was placed inside container 14, in parallel to and spaced 2 mm from counter electrode 24. Proton concentration sensor 32 (Orion 9863BN, Thermo Fisher Scientific Inc., Waltham, Mass., USA) was placed on the wall of cell 12 opposite counter electrode 24, inside volume 30.

Container 14 was filled with an electrolyte solution of 0.1 M $Na_2SO_4$ in water. Proton concentration sensor 32 was connected to a suitable display device to indicate what proton concentration was measured by that sensor in volume 30.

Device 60 was used produce a specified proton concentration in an environment held in volume 30. Counter electrode 24 and working electrode 26 were functionally associated with a variable power supply to establish an electrical circuit. The variable power supply was used to pass a current of between about 0 and about 1 mA $cm^{-2}$ at a potential of between about 0 and about 5V through the electrical circuit including the electrodes. The current passing through the circuit led to hydrolysis of water and the generation of protons and hydroxyl anions in the volume of electrolysis chamber 28. The concentration of protons increased in proximity of the cathode while the concentration of protons decreased in proximity of the anode. Since working electrode 26 was made of mesh and therefore permeable to ions, generated ions from the vicinity of a working electrode 26 passed through working electrode 26 into the electrolyte solution held in volume 30.

Figure 8A:
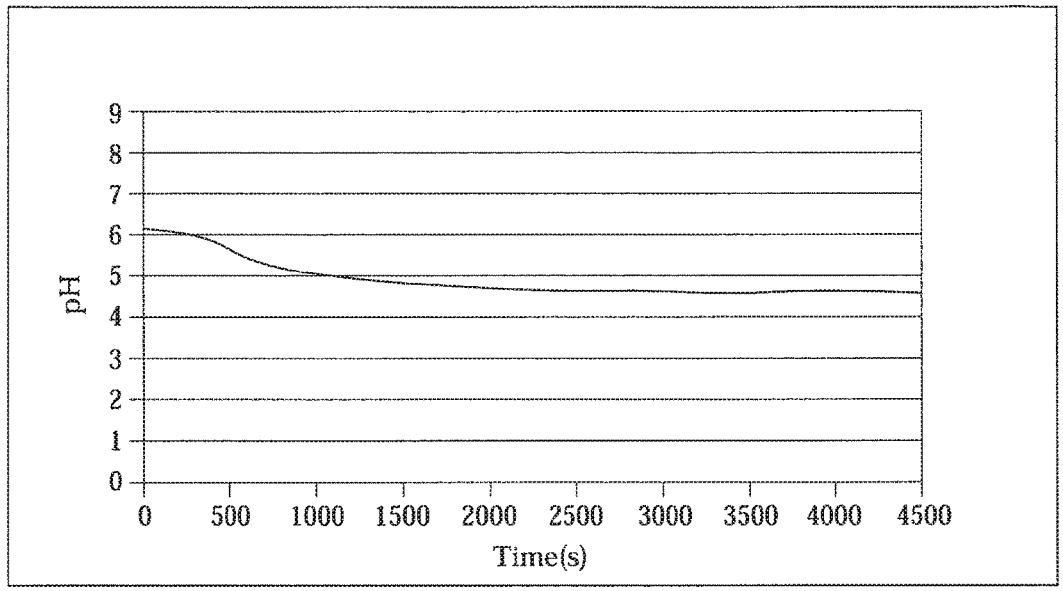
FIGS. 8A-8B are graphs showing proton concentrations produced using the device depicted in FIG. 7A.

The magnitude of the current passing through the circuit was adjusted with reference to the readings of proton concentration sensor 32 until a proton concentration corresponding to a pH of 4.7 was produced in the electrolyte solution held in volume 30, see FIG. 8A.

Figure 8B:
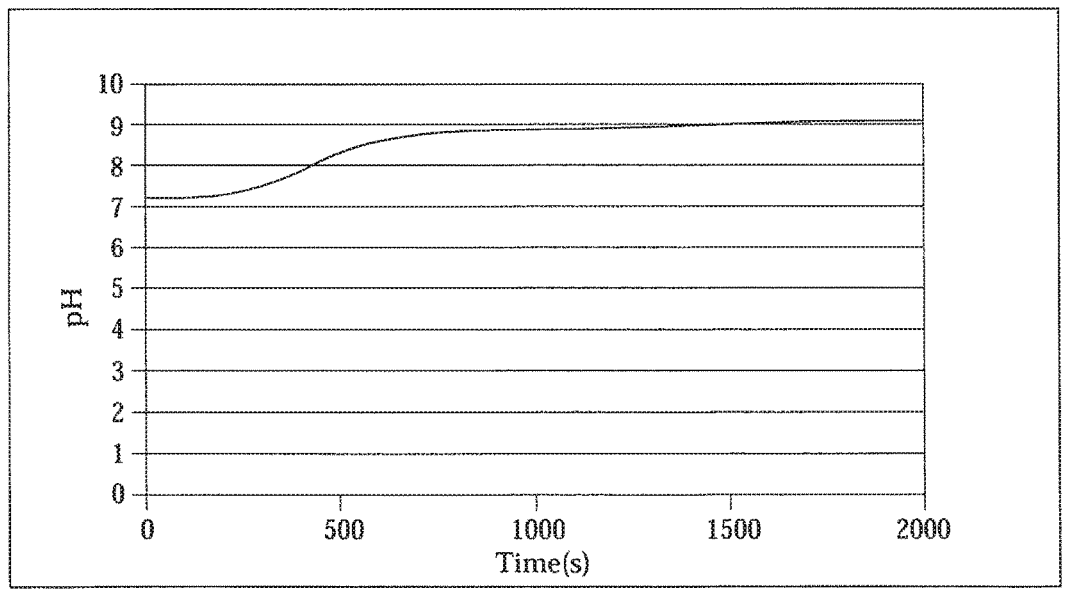

The magnitude of the current passing through the circuit was subsequently adjusted with reference to the readings of proton concentration sensor 32 until a proton concentration corresponding to a pH of 9 was produced in the electrolyte solution held in volume 30, see FIG. 8B.

Device for Producing a Specified Proton Concentration Topography

Figure 7B:
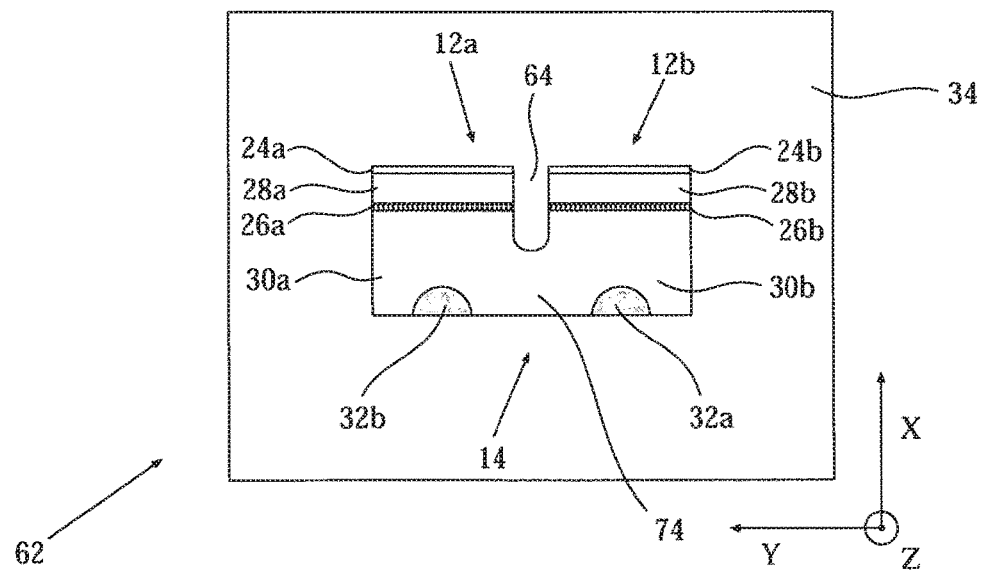

An embodiment of a device for the production of a proton concentration topography in a liquid environment, device 62 was made and used in accordance with the teachings of the invention to produce a specified proton concentration topography. Device 62 is schematically depicted in FIG. 7B in top view.

Casing 34 of device 60 is a block of polymethyl(methacrylate) (Perspex®) 4 cm long (y dimension), 3 cm wide (x dimension) and 2 cm high (z dimension) in which a container 14 was hollowed to accommodate two cells 12a and 12b, each for producing a specified proton concentration in an environment including an electrolyte, each cell 12a or 12b being 1 cm long (y dimension), 0.6 cm wide (x dimension) and 1 cm deep (z dimension). Separating the hollows of container 14 corresponding to each cell 12a and 12b is a 0.2 cm wide (x dimension) impermeable wall 64. Counter electrodes 24a and 24b of 0.1 mm thick platinum mesh were placed along a wall of cell 12a and 12b respectively. Working electrodes 26a and 26b were placed inside container 14, in parallel to and spaced 2 mm from counter electrodes 24a and 24b, proton concentration sensors 32a and 32b (Orion 9863BN, Thermo Fisher Scientific Inc., Waltham, Mass., USA) were placed on the walls of cells 12a and 12b opposite counter electrodes 24a and 24b, inside volumes 30a and 30b.

Container 14 was filled with an electrolyte solution of 0.1 M $Na_2SO_4$ in water. Each proton concentration sensor 32a and 32b was connected to a suitable display device to indicate what pH was measured by that sensor in a corresponding volume 30a or 30b.

Device 62 was used to produce a specified proton concentration topography in the electrolyte solution in a portion of container 14 including volume 30a, 30b and the interface volume 74 there between.

Two electrical circuits were established, each circuit including an electrode pair 24a/26a or 24b/26b and a separate independent variable power supply. Each variable power supply was used to independently pass a current of between about 0 and about 1 mA $cm^{-2}$ at a potential of between about 0 and about 5V through a respective electrical circuit. The current passing through the circuit led to hydrolysis of water and the generation of protons and hydroxyl anions in the volume of electrolyte chamber 28a or 28b. The concentration of protons increased in proximity of the cathode while the concentration of protons decreased in proximity of the anode. Since working electrodes 26a and 26b were of mesh and therefore permeable to ions, generated ions passed from the vicinity of a working electrode 26 through the working electrodes 26 into the electrolyte solution held in a respective associated volume 30a or 30b.

Figure 8C:
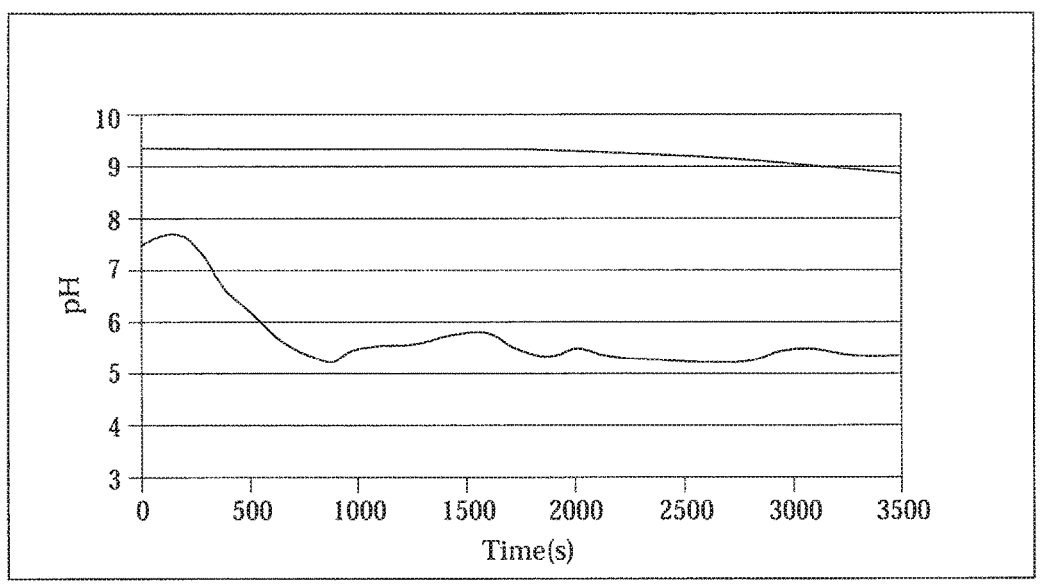
FIG. 8C is a graphs showing a proton concentration topography produced using the device depicted in FIG. 7B.

The current applied between counter electrode 24a and working electrode 26a was adjusted with reference to the readings of proton concentration sensor 32a until a proton concentration corresponding to a pH of 5.2 was measured in the electrolyte solution held in volume 30a associated with working electrode 26a while the current applied between counter electrode 24b and working electrode 26b was adjusted with reference to the readings of proton concentration sensor 32b until a proton concentration corresponding to a pH of 9 was measured in the electrolytic solution held in volume 30b associated with working electrode 26b, see FIG. 8C.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the invention.

Section headings are used herein to ease understanding of the specification and should not be construed as necessarily limiting.

What is claimed is:

1. A method of producing a specified proton concentration topography in an environment including an electrolyte, comprising:
   providing a plurality of independently controllable cells, each cell comprises a counter electrode, a working electrode, an electrolysis volume between said counter electrode and a first side of said working electrode, and a second volume on a second side of said working electrode opposite to said first side, each cell configured to produce a specified proton concentration in said second volume;
   filling said electrolysis volume and said second volume of each of said plurality of cells with an environment including an electrolyte;
   specifying a desired proton concentration topography; and
   activating each said cell of said plurality of cells, so as to produce a specified proton concentration in each said second volume of said environment wherein said specified proton concentrations generated in each said second volume collectively constitute the specified proton concentration topography.

2. The method of claim 1, further comprising:
   specifying a desired newly specified proton concentration topography different than a previously defined proton concentration topography; and
   activating a said cell of said plurality of cells, to produce a different proton concentration in a said second volume of said environment thereby changing said proton concentration topography to be said newly specified proton concentration topography.

3. The method of claim 1, further comprising:
   changing a proton concentration in at least one said associated second volume as a function of time, thereby changing said proton concentration topography as a function of time.

4. The method of claim 1, wherein movement of ions between two neighboring second volumes is substantially uninhibited.

5. The method of claim 1, wherein said activating comprises independently varying a magnitude of each of a plurality of individually controllable electrical currents to produce said desired proton concentration topography, each one of said plurality of individually controllable electrical currents is passed between each said working electrode and each said counter electrode.

6. The method of claim 5, wherein each said working electrode and each said cell of said plurality of independently controllable cells are between said counter electrode and said environment.

7. The method of claim 5, wherein each said working electrode is permeable to a passage of electrolysis products therethrough.

8. The method of claim 1, further comprising:
   monitoring said proton concentration in each said second volume; and
   adjusting a current passing between a respective working electrode located in a respective said independently controllable cell and a respective counter electrode so as to maintain said proton concentration.

9. The method of claim 5, further comprising: changing said plurality of individually controllable electrical currents as a function of time, thereby changing said specified proton concentration in each said second volume of said environment as a function of time.

* * * * *